(12) United States Patent
Butler

(10) Patent No.: US 12,076,174 B2
(45) Date of Patent: Sep. 3, 2024

(54) METHODS FOR ANGIOGRAPHY

(71) Applicant: William E. Butler, Boston, MA (US)

(72) Inventor: William E. Butler, Boston, MA (US)

(*) Notice: Subject to any disclaimer, the term of this patent is extended or adjusted under 35 U.S.C. 154(b) by 11 days.

(21) Appl. No.: 16/784,073

(22) Filed: Feb. 6, 2020

(65) Prior Publication Data

US 2020/0245961 A1 Aug. 6, 2020

Related U.S. Application Data

(60) Provisional application No. 62/801,780, filed on Feb. 6, 2019.

(51) Int. Cl.
*A61B 6/00* (2024.01)
*A61B 6/50* (2024.01)

(52) U.S. Cl.
CPC .............. *A61B 6/481* (2013.01); *A61B 6/503* (2013.01); *A61B 6/504* (2013.01); *A61B 6/5205* (2013.01); *A61B 6/5217* (2013.01); *A61B 6/5258* (2013.01)

(58) Field of Classification Search
CPC .......... A61B 6/481; A61B 6/503; A61B 6/504
See application file for complete search history.

(56) References Cited

U.S. PATENT DOCUMENTS 3,335,716 A 8/1967 Alt et al.
5,628,980 A 5/1997 Ranganathan et al.
(Continued)

FOREIGN PATENT DOCUMENTS

CN 101406392 B 5/2011
CN 108665449 A 10/2018
(Continued)

OTHER PUBLICATIONS

Nyqvist, H., "Certain Topics in Telegraph Transmission Theory," Transactions of the AIEE, vol. 47, pp. 617-644, 1928 (28 pages).
(Continued)

*Primary Examiner* — Joel Lamprecht
*Assistant Examiner* — Milton Truong
(74) *Attorney, Agent, or Firm* — Jason M. Shapiro; Devlin Law Firm LLC

(57) ABSTRACT

An angiogram is a study of blood vessels where an angiographic chemical contrast agent is injected while a sequence of images (typically x-rays) are obtained. The contrast pattern on the sequence of images provides information about the vascular anatomy and physiology. The discovery that contrast in blood vessels varies at cardiac frequency in magnitude and phase, which may be visualized as a spatiotemporal reconstruction of cardiac frequency angiographic phenomena, enables a set of processes for increasing the signal to noise ratio or equivalently the informational content of an angiogram. In this invention, the organization of cardiac frequency magnitude and phase enables equivalent information on anatomy and physiology to be obtained with less dose of injected chemical contrast agent, less x-ray dose, and/or less navigation of the injecting catheter within blood vessels. The cardiac frequency magnitude and phase is organized so that the arterial and venous subsystems of circulation have coherence at cardiac frequency. This enables processes for diagnosing deficits of circulation that involve alterations in the transit of blood from the arterial to the venous subsystems of circulation. Furthermore, the discovery of cardiac frequency magnitude and phase organization enables the design and manufacture of lighter and more portable angiography equipment.

21 Claims, 8 Drawing Sheets

(56) References Cited

U.S. PATENT DOCUMENTS

| | | | |
|---|---|---|---|
| 5,637,871 A | 6/1997 | Piety et al. | |
| 5,963,676 A | 10/1999 | Wu et al. | |
| 6,195,456 B1 | 2/2001 | Balasubramanian et al. | |
| 6,442,414 B1 | 8/2002 | Watanabe | |
| 6,549,801 B1 | 4/2003 | Chen et al. | |
| 6,842,638 B1 | 1/2005 | Suri et al. | |
| 6,975,753 B2 | 12/2005 | Matsuura et al. | |
| 6,985,632 B2 | 1/2006 | Sato et al. | |
| 7,020,314 B1 | 3/2006 | Suri et al. | |
| 7,035,679 B2 | 4/2006 | Addison et al. | |
| 7,201,892 B2 | 4/2007 | Achilefu et al. | |
| 7,359,062 B2 | 4/2008 | Chen et al. | |
| 7,602,183 B2 | 10/2009 | Lustig et al. | |
| 8,244,334 B2 | 8/2012 | Huang et al. | |
| 8,306,295 B2 | 11/2012 | Bruder et al. | |
| 8,306,303 B2 | 11/2012 | Bruder et al. | |
| 8,417,048 B2 | 4/2013 | Reboni et al. | |
| 8,559,692 B2 | 10/2013 | Reboni et al. | |
| 8,605,976 B2 | 12/2013 | Diamant et al. | |
| 8,611,633 B2 | 12/2013 | Kwon et al. | |
| 8,628,751 B2 | 1/2014 | Neumann et al. | |
| 8,948,480 B2 | 2/2015 | Liu et al. | |
| 9,019,305 B2 | 4/2015 | Baumgart et al. | |
| 9,036,780 B2 | 5/2015 | Kyriakou et al. | |
| 9,165,349 B2 | 10/2015 | Kwon et al. | |
| 9,324,005 B2 | 4/2016 | Wadhwa et al. | |
| 9,345,413 B2 | 5/2016 | Schie et al. | |
| 9,357,916 B2 | 6/2016 | Srivastava et al. | |
| 9,811,901 B2 | 11/2017 | Wu et al. | |
| 9,814,384 B2 | 11/2017 | Schmoll | |
| 9,836,849 B2 | 12/2017 | Dickrell, III et al. | |
| 9,962,124 B2 | 5/2018 | Najarian et al. | |
| 10,123,761 B2 | 11/2018 | Butler | |
| 10,226,176 B2 | 3/2019 | Schmoll | |
| 10,299,677 B2 | 5/2019 | Spaide | |
| 10,653,379 B2 | 5/2020 | Rapoport | |
| 11,386,563 B2 | 7/2022 | Figueroa-Alvarez et al. | |
| 2004/0101090 A1* | 5/2004 | Drummond | A61B 6/504 378/4 |
| 2004/0254523 A1* | 12/2004 | Fitzgerald | A61M 1/3609 604/35 |
| 2005/0080327 A1 | 4/2005 | Jenkins et al. | |
| 2007/0106146 A1 | 5/2007 | Altmann et al. | |
| 2007/0106149 A1 | 5/2007 | Mistretta | |
| 2007/0185393 A1 | 8/2007 | Zhou et al. | |
| 2008/0045847 A1 | 2/2008 | Farag et al. | |
| 2008/0226149 A1 | 9/2008 | Wischmann et al. | |
| 2010/0113949 A1 | 5/2010 | Sathyanarayana | |
| 2010/0272184 A1 | 10/2010 | Fishbain et al. | |
| 2011/0142288 A1 | 6/2011 | Diamant et al. | |
| 2012/0134553 A1 | 5/2012 | Liao et al. | |
| 2013/0101187 A1 | 4/2013 | Sundar et al. | |
| 2013/0116554 A1* | 5/2013 | Kaiser | A61K 49/0438 600/425 |
| 2013/0243348 A1* | 9/2013 | Goshen | G06T 5/20 382/274 |
| 2014/0005563 A1 | 1/2014 | Ramanathan et al. | |
| 2014/0044330 A1 | 2/2014 | Klingenbeck | |
| 2014/0072190 A1 | 3/2014 | Wu et al. | |
| 2014/0072228 A1 | 3/2014 | Rubinstein et al. | |
| 2014/0072229 A1 | 3/2014 | Wadhwa et al. | |
| 2014/0378795 A1 | 12/2014 | McKenna | |
| 2015/0045684 A1 | 2/2015 | Schie | |
| 2015/0190533 A1* | 7/2015 | Newton | A61B 6/032 424/9.452 |
| 2015/0257653 A1 | 9/2015 | Hyde et al. | |
| 2016/0135775 A1 | 5/2016 | Mistretta et al. | |
| 2016/0189394 A1 | 6/2016 | Zhang et al. | |
| 2016/0220112 A1 | 8/2016 | Schmoll | |
| 2016/0267704 A1 | 9/2016 | Mistretta et al. | |
| 2016/0349346 A1 | 12/2016 | Cheng | |
| 2017/0000441 A1* | 1/2017 | Butler | A61B 6/481 |
| 2017/0367603 A1 | 12/2017 | Spector | |
| 2018/0040147 A1* | 2/2018 | Alhrishy | A61B 6/5205 |
| 2018/0047160 A1 | 2/2018 | Wu et al. | |
| 2018/0055471 A1 | 3/2018 | Redel | |
| 2019/0015061 A1 | 1/2019 | Liebeskind et al. | |
| 2019/0046147 A1 | 2/2019 | Butler | |
| 2019/0053780 A1 | 2/2019 | Song et al. | |
| 2019/0159707 A1 | 5/2019 | Albuquerque et al. | |
| 2019/0343383 A1 | 11/2019 | Spaide | |
| 2020/0193597 A1 | 6/2020 | Fan et al. | |
| 2020/0245965 A1 | 8/2020 | Butler | |
| 2020/0286237 A1 | 9/2020 | Butler | |
| 2020/0305822 A1 | 10/2020 | Butler | |
| 2020/0320710 A1 | 10/2020 | Butler | |
| 2020/0397396 A1 | 12/2020 | Butler | |
| 2021/0137634 A1* | 5/2021 | Lang | A61B 90/13 |
| 2023/0316514 A1 | 10/2023 | Butler et al. | |

FOREIGN PATENT DOCUMENTS

| | | |
|---|---|---|
| EP | 1322219 B1 | 5/2007 |
| EP | 2693401 A1 | 2/2014 |
| JP | 2004-174262 A | 6/2004 |
| WO | 2014/162273 A1 | 10/2014 |
| WO | 2020163614 A1 | 8/2020 |
| WO | 2020163629 A1 | 8/2020 |
| WO | 2020185706 A1 | 9/2020 |
| WO | 2020198592 A1 | 10/2020 |
| WO | 2020206430 A1 | 10/2020 |

OTHER PUBLICATIONS

Kotelnikov, V.A., "On the transmission capacity of the 'ether' and of cables in electrical communications," Proceedings of the first All-Union Conference on the technological reconstruction of the communications sector and the development of low-current engineering, Moscow, 1933 (23 pages).

Shannon, C.E., "Communication in the Presence of Noise," Proceedings of the Institute of Radio Engineers, vol. 37, No. 1, pp. 10-21, 1949 (11 pages).

Butler, W.E., "Wavelet brain angiography suggests arteriovenous pulse wave phase locking," PLOS ONE, Nov. 15, 2017 (16 pages).

Sagel, S.S., "Gated Computed Tomography of the Human Heart," Investigative Radiology, vol. 12, No. 6, pp. 563-566, 1977 (4 pages).

Wikipedia article "Dose Area Product" accessed online on Jun. 15, 2020 at: <https://en.wikipedia.org/wiki/Dose_area_product> (2 pages).

International Search Report and Written Opinion received in related application No. PCT/US20/17037, dated May 7, 2020 (12 pages).

Anonymous, Artis Zeego, Data Sheet VC21, Multi-axis for interventional imaging, Oct. 2014, 36 pages, www.siemens.com/healthcare.

Babin et al., Segmentation and length measurement of the abdominal blood vessels in 3-D MRI images, Conference Proceedings IEEE Engineering in Medicine and Biology Society, Sep. 2-6, 2009, pp. 4399-4402.

Barfett et al., Intra-vascular blood velocity and volumetric flow rate calculated from dynamic 4D CT angiography using a time of flight technique, The International Journal of Cardiovascular Imaging, Oct. 2014, vol. 30(7), pp. 1383-1392.

Bhadelia et al., Cerebrospinal fluid pulsation amplitude and its quantitative relationship to cerebral blood flow pulsations: a phase-contrast MR flow imaging study, Neuroradiology, Apr. 1997, vol. 39(4), pp. 258-264.

Long et al., Spatiotemporal wavelet analysis for functional MRI, NeuroImage, Oct. 2004, vol. 23(2), pp. 500-516.

Daubechies, The wavelet transform, time-frequency localization, and signal analysis, IEEE Transactions on Information Theory, Sep. 1990, vol. 36, iss. 5, pp. 961-1005.

Gabor, Theory of communication. Part I: The analysis of information, Journal of the Institution of Electrical Engineers—Part III: Radio and Communication Engineering, Nov. 1946, vol. 93(26), pp. 429-441.

Goupillaud et al., Cycle-octave and related transforms in seismic signal analysis, Geoexploration, Oct. 1984, vol. 23, iss. 1, pp. 85-102.

(56) References Cited

OTHER PUBLICATIONS

Kuroiwa et al., Development and clinical application of near-infrared surgical microscope: preliminary report, Minimally invasive neurosurgery: MIN, Dec. 2001, vol. 44(4), pp. 240-242.
Markl et al., 4D Flow MRI, Journal of Magnetic Resonance Imaging (JMRI), Oct. 2012, vol. 36, iss. 5, pp. 1015-1036.
Moser et al., On the accuracy of EPI-based phase contrast velocimetry, Magnetic Resonance Imaging, Nov. 2000, vol. 18, iss. 9, pp. 1115-1123.
Persson et al., Hydrocephalus prevalence and outcome in a population-based cohort of children born in 1989-1998, Acta Paediatrica, Jun. 2005, vol. 94, iss. 6, pp. 726-732.
Provost et al., 3D Ultrafast ultrasound imaging in vivo, Physics in Medicine and Biology, Sep. 10, 2014, vol. 59, iss. 19, L1-L13.
Raabe et al., Prospective evaluation of surgical microscope-integrated intraoperative near-infrared indocyanine green videoangiography during aneuryism surgery, Journal of Neurosurgery, Dec. 2005, vol. 103, iss. 6, pp. 982-989.
Rao et al., Shear strain imaging using shear deformations, Med Phys., Feb. 2008, vol. 35(2), pp. 412-423.
Rasul et al., Is endoscopic third ventriculostomy superior to shunts in patients with non-communicating hydrocephalus? A systematic review and meta-analysis of the evidence, Acta Neurochirurgica, May 2013, vol. 155, iss. 5, pp. 883-889.
Sugawara et al., Arterial path length measurements required for the pulse wave velocity, Journal of Hypertension, May 2009, vol. 27, iss. 5, pp. 1102-1104.
Tomita et al., Automated method for tracking vast numbers of FITC-labeled RBCs in microvessels of rat brain in vivo using a high-speed confocal microscope system, Microcirculation, Feb. 2008, vol. 15, iss. 2, pp. 163-174.
Unser, Sampling—50 years after Shannon, Proceedings of the IEEE, Apr. 2000, vol. 88, No. 4, pp. 569-587.
Wagshul et al., The pulsating brain: A review of experimental and clinical studies of intracranial pulsatility, Fluids and Barriers of the CNS, Jan. 18, 2011, vol. 8, iss. 5, pp. 1-23.
Weaver et al., Brain mechanical property measurement using MRE with intrinsic activation, Physics in Medicine Biology, Nov. 2012, vol. 57, No. 22, pp. 7275-7287.
Zaidi et al., Indocyanine Green Angiography in the Surgical Management of Cerebral Arteriovenous Malformations: Lessons Learned in 130 Consecutive Cases, Operative Neurosurgery, Jun. 2014, vol. 10, No. 2, pp. 246-251.
Zou et al., Intracranial pressure waves: characterization of a pulsation absorber with notch filter properties using systems analysis, J. Neurosurg Pediatrics, Jul. 2008, vol. 2(1), pp. 83-94.
Henneman et al., Phase analysis of gated myocardial perfusion single-photon emission computed tomography compared with tissue doppler imaging for the assessment of left ventricular dyssynchrony, Journal of the American College of Cardiology, Apr. 2007, vol. 49 (16), pp. 1708-1714.
Kingdom et al., Sensitivity to contrast histogram differences in synthetic wavelet-textures, Vision Research, Mar. 2001, vol. 41(5), pp. 585-598.
Li et al., Cross-frequency coupling during isoflurane anaesthesia as revealed by electroencephalographic harmonic wavelet bicoherence, Neurosciences and Neuroanaesthesia, British Journal of Anaesthesia, Mar. 2013, vol. 110(3), pp. 409-419.
Moore, A modification of the Rayleigh test for vector data, Biometrika, Apr. 1980, vol. 67(1), pp. 175-180.
Mousavi et al., A wavelet transform based method to determine depth of anesthesia to prevent awareness during general anesthesia, Computational and Mathematical Methods in Medicine, 2014, vol. 2014, pp. 1-13.
Rakhmanov et al., A cross-correlation method for burst searches with networks of misaligned gravitational-wave detectors, Institute of Physics Publishing, Classical and Quantum Gravity, Sep. 6, 2005, vol. 22(18), pp. S1311-S1320.
Wang et al., The residual phase estimation of a seismic wavelet using a renyi divergence-based criterion, Journal of Applied Geophysics, Jul. 2014, vol. 106, pp. 96-105.
Yu, Histogram Matching Seismic Wavelet Phase Estimation, May 2012, Masters thesis, University of Houston.
Anor et al., Modeling of blood flow in arterial trees, Focus Article, WIREs Systems Biology and Medicine, Sep./Oct. 2010, vol. 2, pp. 612-623.
Hamberg et al., Quantitative high-resolution measurement of cerebrovascular physiology with slip-ring CT, AJNR Am J Neuroradiol, Apr. 1996, vol. 17(4), pp. 639-650.
Kashif et al., Model-based non-invasive estimation of intracranial pressure from cerebral blood flow velocity and arterial pressure, Science Translational Medicine, Apr. 2012, vol. 4(129): 129ra44.
Lassen et al., Tracer Kinetic Methods in Medical Physiology, 1979, Raven Press, New York.
Linninger et al., A mathematical model of blood, cerebrospinal fluid and brain dynamics, J Mathematical Biology, Dec. 2009, vol. 59(6), pp. 729-759.
Bayer et al., Two-dimensional simulations of displacement accumulation incorporating shear strain, Ultrason Imaging, Jan. 2014, vol. 36(1), pp. 55-73.
Braun et al., High-resolution mechanical imaging of the human brain by three-dimensional multifrequency magnetic resonance elastography at 7T, NeuroImage, Apr. 2014, vol. 90, pp. 308-314.
Feingold et al., Quantitative volumetric perfusion mapping of the microvasculature using contrast ultrasound, Invest Radiol, Oct. 2010, vol. 45(10), pp. 669-674.
Gauthier et al., Assessment of quantitative perfusion parameters by dynamic contrast-enhanced sonography using a deconvolution method, an in vitro and in vivo study, J Ultrasound Med, Apr. 2012, vol. 31(4), pp. 595-608.
Johnson et al., Local mechanical properties of white matter structures in the human brain, NeuroImage, Oct. 2013, vol. 79, pp. 145-152.
Ashmead, Morelet Wavelets in quantum mechanics, Quanta, Nov. 2012, vol. 1, Issue 1, pp. 58-70.
Johnstone et al., Wavelet threshold estimators for data with correlated noise, Journal of the Royal Statistical Society: Series B (Statistical Methodology), 1997, 59(2), pp. 319-351.
Khullar et al., Wavelet-based fMRI analysis: 3-d denoising, signal separation, and validation metrics, NeuroImage, Feb. 2011, vol. 54(4), pp. 2867-2884.
Forbes et al., Statistical Distributions, Fourth Edition, copyright 2011, John Wiley and Sons, Inc., Chapters 1-9, (84 pages).
Mandelshtam et al., Harmonic inversion of time signals and its applications, AIP The Journal of Chemical Physics 1997, vol. 107, No. 6756, 12 pages.
Schroeder, The Simple Harmonic Oscillator, copyright 2015-2016, 5 pages (https://physics.weber.edu/schroeder/quantum/Harmonic.pdf).
International Standards Organization, ISO/IEC 14496-12 Multimedia Formats Information Technology—Coding of audio-visual objects (2008) 4 pages (Abstract).
Guido et al., Introduction to the special issue on wavelet-based algorithms for medical problems (2007) vol. 37, p. 429.
Candes et al., New Tight Frames of Curvelets and Optimal Representations of Objects with C2 Singularities, Nov. 2002, pp. 1-39 (http://citeseerx.ist.psu.edu/viewdoc/download?doi=10.1.1.162.1548&rep=rep1&type=pdf).
Cense et al., Ultrahigh-resolution high-speed retinal imaging using spectral-domain optical coherence tomography, Optics Express, May 31, 2004, vol. 12, No. 11, pp. 2435-2447 (13 pages).
Cheng et al., Mammalian DNA Methyltransferases: A Structural Perspective, Structure, Review, Mar. 2008, vol. 16, No. 3, pp. 341-350.
Coumans et al., Volumetric analysis of syringomyelia following hindbrain decompression for Chiari malformation Type I: syringomyelia resolution follows exponential kinetics, Neurosurg Focus, Sep. 2011, vol. 31, No. 3:E4, pp. 1-4.
Dahmen, Wavelet and Multiscale Methods for Operator Equations, 1997 (146 pages).

(56) References Cited

OTHER PUBLICATIONS

Deutsch et al., Information Flow in Entangled Quantum Systems, (1999) pp. 1-24 (https://arxiv.org/ftp/quant-ph/papers/9906/9906007.pdf).

Donoho, Compressed Sensing, Sep. 14, 2004, pp. 1-34.

Donoho et al., Message-Passing Algorithms for Compressed Sensing, PNAS, Nov. 10, 2009, vol. 106, No. 45, pp. 18914-18919.

Duverger et al., Concentrations of Putative Neurovascular Transmitters in Major Cerebral Arteries and Small Pial Vessels of Various Species, Journal of Cerebral Blood Flow and Metabolism, 1987, vol. 7, No. 4, pp. 497-501.

Eastwood, The Penrose Transform for Complex Projective Space, Cornell University Archive, Aug. 17, 2008, pp. 1-11 (https://arxiv.org/abs/0808.2321, arXiv:0808.2321v1).

Eastwood et al., Cohomology and Massless Fields, Commun. Math. Phys. (1981) vol. 78, pp. 305-351.

Edelman et al., Nitric Oxide: Linking Space and Time in the Brain, Proc. Natl. Acad. Sci. USA, Dec. 1992, vol. 89, pp. 11651-11652.

Feichtinger et al., Gabor Frames and Time-Frequency Analysis of Distributions, Journal of Functional Analysis, 1997, vol. 146, No. FU963078, pp. 464-495.

Feng et al., Conservation and Divergence of Methylation Patterning in Plants and Animals, PNAS, May 11, 2010, vol. 107, No. 19, pp. 8689-8694.

Fisher et al., Group Formation, Relatedness, and the Evolution of Multicellularity, Current Biology, Jun. 17, 2013, vol. 23, No. 12, pp. 1120-1125.

Fujimoto et al., Optical Coherence Tomography: An Emerging Technology for Biomedical Imaging and Optical Biopsy, Neoplasia, Jan.-Apr. 2000, vol. 2, Nos. 1-2, pp. 9-25.

Goriely et al., Mechanics of the brain: perspectives, challenges, and opportunities, Biomech Model Mechanobiol, 2015, vol. 14, pp. 931-965.

Guerquin-Kern et al., A Fast Wavelet-Based Reconstruction Method for Magnetic Resonance Imaging, IEEE Transactions on Medical Imaging, Institute of Electrical and Electronics Engineers, 2011, 14 pages (obtained from HAL archives-ouvertes).

Guo et al., Sparse Multidimensional Representations using Anisotropic Dilation and Shear Operators, 2005, 13 pages (https://www.math.uh.edu/~dlabate/Athens.pdf).

Han, Properties of Discrete Framelet Transforms, Math. Model. Nat. Phenom., 2013, vol. 8, No. 1, pp. 18-47 (32 pages).

Heil, What is a Frame?, Notices of the AMS, 2013, vol. 60, No. 6, pp. 748-750.

Herz et al., Ultrahigh resolution optical biopsy with endoscopic optical coherence tomography, Optics Express, Jul. 26, 2004, vol. 12, No. 15, pp. 3532-3542.

Hogeweg, Cellular Automata as a Paradigm for Ecological Modeling, Applied Mathematics and Computation, 1988, vol. 27, pp. 81-100.

Hormander, The Spectral Function of an Elliptic Operator, Acta Math, May 7, 1968, vol. 121, pp. 193-218.

Huff et al., Dnmt1-Independent CG Methylation Contributes to Nucleosome Positioning in Diverse Eukaryotes, Cell, Mar. 13, 2014, vol. 156, No. 6, pp. 1286-1297.

Januszewski et al., Flow-based evalution of cerebral revascularization using near-infrared indocyanine green videoangiography, Neurosurg Focus, Feb. 2014, vol. 36, No. 2: E14, pp. 1-8.

Jia et al., Quantitative OCT angiography of optic nerve head blood flow, Biomedical Optics Express, Dec. 1, 2012, vol. 3, No. 12, pp. 3127-3137.

Kamble et al., A Review: Eulerian Video Motion Magnification, International Journal of Innovative Research in Computer and Communication Engineering, Mar. 2015, vol. 3, iss. 3, pp. 2384-2390.

Kim et al., Epigenetic mechanisms in mammals, Cellular and Molecular Life Sciences, 2009, vol. 66, pp. 596-612.

Kittipoom et al., Construction of Compactly Supported Shearlet Frames, Cornell University Archive, 2010, pp. 1-37 (https://arxiv.org/abs/1003.5481, arXiv:1003.5481v2).

Klimenko et al., A cross-correlation technique in wavelet domain for detection of stochastic gravitational waves, 2002, pp. 1-15 (https://arxiv.org/abs/gr-qc/0208007, arXiv:gr-qc/0208007v1).

Knopfmacher et al., Graphs, partitions and Fibonacci numbers, Discrete Applied Mathematics, 2007, vol. 155, pp. 1175-1187.

Koenig et al., Regression of Subependymal Giant Cell Astrocytoma With Rapamycin in Tuberous Sclerosis Complex, J Child Neurol., Oct. 2008, vol. 23, No. 10, pp. 1238-1239.

Kramer et al., Intraventricular fibrinolysis with tissue plasminogen activator is associated with transient cerebrospinal fluid inflammation: a randomized controlled trial, Journal of Cerebral Blood Flow & Metabolism, 2015, vol. 35, pp. 1241-1248.

Kutyniok et al., Resolution of the Wavefront Set using Continuous Shearlets, Transactions of the American Mathematical Society, May 2009, vol. 361, No. 5, pp. 2719-2754.

Kutyniok et al., Image Separation using Wavelets and Shearlets, International Conference on Curves and Surfaces, 2010, pp. 1-14 (https://www.math.tu-berlin.de/fileadmin/i26_fg-kutyniok/Kutyniok/Papers/ImageSeparation.pdf).

Lee, Wavelet-Vaguelette Decompositions and Homogeneous Equations, Dec. 1997, Purdue University, In Partial Fulfillment of the Requirements for the Degree of Doctor of Philosophy, 103 pages.

Lindenmayer, Developmental Algorithms for Multicellular Organisms: A Survey of L-Systems, J. Theor. Biol., 1975, vol. 54, pp. 3-22.

Lopez et al., The Cauchy problem for a forced harmonic oscillator, Revista Mexicana De Fisica, Dec. 2009, vol. 55, No. 2, pp. 196-215.

Luney et al., Acute Posterior Cranial Fossa Hemorrhage—Is Surgical Decompression Better than Expectant Medical Management?, Neurocritical Care, Apr. 12, 2016, 6 pages.

Makita et al., Optical Coherence Angiography, Optics Express, Aug. 21, 2006, vol. 14, No. 17, pp. 7821-7840.

Gabor, Theory of Communication, Part 3: Frequency Compression and Expansion, 1946, vol. 93, No. 26, pp. 445-457.

Tavla et al., Wavelet-based calculation of cerebral angiographic data from time-resolved CT perfusion acquisitions, Eur Radiol. Aug. 2015, vol. 25, No. 8, pp. 2354-2361 (published online Feb. 26, 2015) (8 pages).

Kamp et al., Microscope-Integrated Quantitative Analysis of Intraoperative Indocyanine Green Fluorescence Angiography for Blood Flow Assessment: First Experience in 30 Patients, Operative Neurosurgery 1, vol. 70, Mar. 2012, pp. ons65-ons74.

Mazzola et al., Pediatric Hydrocephalus: systematic literature review and evidence-based guidelines. Part 2: Management of posthemorrhagic hydrocephalus in premature infants, Nov. 2014, J Neurosurg Pediatrics (Suppl), vol. 14, pp. 8-23.

McCrory et al., Consensus statement on concussion in sport: the 4th International Conference on Concussion in Sport held in Zürich, Nov. 2012, Br J Sports Med, (2013), vol. 47, pp. 250-258.

Michod et al., Cooperation and Conflict in the Evolution of Multicellularity, 2001, The Genetics Society of Great Britain, Heredity, vol. 86, pp. 1-7.

Nehra et al., Peyronie's Disease: AUA Guideline, American Urological Association (AUA) Guideline, approved Apr. 2015, pp. 1-41.

Kritika Iyer, et al., "AngioNet: a convolutional neural network for vessel segmentation in X-ray angiography", Scientific Reports, www.nature.com/scientificreports/, (2021) 11:18066, https://doi.org/10.1038/s41598-021-97355-8, 13 pages.

Romain Lacroix, "3D Optical flow analysis of a pulsed contrast agent in the bloodstream. Application to virtual angiography and Magnetic Particle Imaging", Medical Imaging, Télécom Bretagne; Université de Bretagne Occidentale, Apr. 5, 2016, English, tel-01298049, https://hal.archives-ouvertes.fr/tel-01298049/document, 48 pages.

Jerome Revaud, et al., "EpicFlow: Edge-Preserving Interpolation of Correspondences for Optical Flow", May 19, 2019, https://arxiv.org/pdf/1501.02565v2.pdf, 11 pages.

Navid Nourani-Vatani, et al., "A Study of Feature Extraction Algorithms for Optical Flow Tracking", Dec. 5, 2012, https://www.araa.asn.au/acra/acra2012/papers/pap105.pdf, 7 pages.

Köse, Cemal, "Fully Automatic Segmentation of Coronary Vessel Structures in Poor Quality X-Ray Angiogram Images," SSPR&SPR 2006, pp. 74-82 (2006).

(56) References Cited

OTHER PUBLICATIONS

Nielsen, Conditions for A Class of Entanglement Transformations, Aug. 17, 1999, pp. 1-4 (Cornell University Archive, arXiv No. quant-ph/9811053v2).
Novotny et al., A Method of Photographing Fluorescence in Circulating Blood in the Human Retina, Circulation, vol. XXIV, Jul. 1961, pp. 82-86.
Pewsey et al., Circular Statistics in R, Oxford University Press, (2013) Chapters 1-3, 7 and Appendix (80 pages).
Pfister et al., Molecular diagnostics of CNS embryonal tumors, Acta Neuropathology, Nov. 2010, vol. 120, No. 5, pp. 553-566.
Pollock, Dyadic Wavelets Analysis, (2016) pp. 1-26.
Qian et al., High Resolution Stationary Digital Breast Tomosynthesis using Distributed Carbon Nanotube X-ray Source Array, Medical Physics, (Apr. 2012) vol. 39, No. 4, pp. 2090-2099.
Rashid-Farrokhi et al., Wavelet-Based Multiresolution Local Tomography, IEEE Transactions on Image Processing, Oct. 1997, vol. 6, No. 10, pp. 1412-1430.
Rollins et al., Real-time in vivo color Doppler optical coherence tomography, Journal of Biomedical Optics, Jan. 2002, vol. 7, No. 1, pp. 123-129.
Ronneberger et al., U-Net: Convolutional Networks for Biomedical Image Segmentation, May 18, 2015, pp. 1-8 (Cornell University Archive, arXiv No. 1505.04597v1).
Ruzhansky, Introduction to pseudo-differential operators, Jan. 21, 2014, pp. 1-54.
Sadowsky, The Continuous Wavelet Transform: A Tool for Signal Investigation and Understanding, John Hopkins APL Technical Digest, 1994, vol. 15, No. 4, pp. 306-318.
Saito et al., Efficient Gene Transfer into the Embryonic Mouse Brain Using in Vivo Electroporation, Developmental Biology, 2001, vol. 240, pp. 237-246.
Sen et al., 3D ROI Image Reconstruction from Truncated Computed Tomogrpahy, IEEE Transactions on Medical Imaging, May 26, 2013, pp. 1-24.
Shen et al., Growth hormone therapy and risk of recurrence/progression in intracranial tumors: a meta-analysis, Neurol Sci, 2015, vol. 36, pp. 1859-1867.
Shy et al., X-Y separable pyramid steerable scalable kernels, (1994) pp. 237-244 (https://authors.library.caltech.edu/3438/1/SHYcvpr94.pdf).
Valens, A Really Friendly Guide to Wavelets, 1999, pp. 1-19.
Vrhel et al., Fast Computation of the Continuous Wavelet Transform through Oblique Projections, (1996) pp. 1-4 (http://citeseerx.ist.psu.edu/viewdoc/download?doi=10.1.1.66.3780&rep=rep1&type=pdf).
Wang et al., Three dimensional optical angiography, Optics Express, Apr. 2, 2007, vol. 15, No. 7, pp. 4083-4097.
Wang et al., Doppler optical micro-angiography for volumetric imaging of vascular perfusion in vivo, May 25, 2009, Optics Express, vol. 17, No. 11, pp. 8926-8940.
Wunsch, Microlocal Analysis and Evolution Equations: Lecture Notes from 2008 CMI/ETH Summer School, 2012 (92 pages).
Yang et al., The X-Ray Transform Projection of 3D Mother Wavelet Function, Research Article, Computational and Mathematical Methods in Medicine, 2013, Article ID 754829, 9 pages.
Zhu et al., Endothelial nitric oxide synthase: a potential therapeutic target for cerebrovascular diseases, Molecular Brain, 2016, vol. 9, No. 30, pp. 1-8.
Zhuang et al., Fan-beam and cone-beam image reconstruction via filtering the backprojection image of differentiated projection data, Institute of Physics Publishing, Physics in Medicine and Biology, 2004, vol. 49, pp. 5489-5503.
Taylor et al., Molecular subgroups of medulloblastoma: the current consensus, Consensus Paper, Acta Neuropathol, 2012, vol. 123, pp. 465-472.
Thavavel et al., Regularized Computed Tomography using Complex Wavelets, International Journal of Magnetic Resonance Imaging, 2007, vol. 01, No. 01, pp. 027-032.
Thielen et al., Ultrafast dynamic computed tomography myelography for the precise identification of high-flow cerebrospinal fluid leaks caused by spiculated spinal osteophytes, J Neurosurg Spine, Clinical Article, Mar. 2015, vol. 22, pp. 324-331.
Spaide et al., Retinal Vascular Layers Imaged by Fluorescein Angiography and Optical Coherence Tomography Angiography, Original investigation, JAMA Opthalmology, Jan. 2015, vol. 133, No. 1, pp. 45-50.
Ren et al., Phase-resolved functional optical coherence tomography: simultaneous imaging of in situ tissue structure, blood flow velocity, standard deviation, birefirngence, and Stokes vectors in human skin, Optics Letters, Oct. 1, 2002, vol. 27, No. 19, pp. 1702-1704.
Shenoi, Introduction to Digital Signal Processing and Filter Design, Wiley, 2006, Chapters 3-5 (217 pages).
Srinivasan et al., Quantitative Cerebral Blood Flow with Optical Coherence Tomography, Optics Express, Feb. 1, 2010, vol. 18, No. 3, pp. 2477-2494.
Steane, An introduction to spinors, Dec. 13, 2013, pp. 1-23 (Cornell University Archive, arXiv No. 1312.3824v1).
Thompson et al., Prognostic Value of Medulloblastoma Extent of Resection After Accounting for Molecular Subgroup: A Retrospective Integrated Clinical and Molecular Analysis, Lancet Oncol. Apr. 2016, vol. 17, No. 4, pp. 484-495.
Timmons, Image-Guided Neurosurgery: Integration of Medical Image Data with a Real-time View of the Surgical Field, Jun. 1997, pp. 1-66.
Tran et al., Learning Spatiotemporal Features with 3D Convolutional Networks, Proceedings of the 2015 IEEE International Conference on Computer Vision (ICCV), (2015) pp. 4489-4497.
Rao et al., Shear strain imaging using shear deformations (2008) Med. Phys. 35(2):412-423.
Weaver et al., Brain mechanical property measurement using MRE with intrinsic activation Phys. Med. Biol. (2012) 57:7275-7287.
Kashif et al., Model-Based Noninvasive Estimation of Intracranial Pressure from Cerebral Blood Flow Velocity and Arterial Pressure, Sci. Transl. Med. (2012) vol. 4, No. 129, pp. 1-10.
Bayer et al., Two-Dimensional Simulations of Displacement Accumulation Incorporating Shear Strain, Ultrason. Imaging (2014) vol. 36(1):55-73.
Feingold et al., Quantitative volumetric perfusion mapping of the microvasculature using contrast ultrasound, Invest Radiol. (2010) 45:669-674.
Johnson et al., Local mechanical properties of white matter structures in the human brain, NeuroImage (2013) 79:145-152.
Khullar et al., Wavelet-based fMRI analysis: 3-D denoising, signal seperation, and validation metrics, NeuroImage (2011) 54:2867-2884.
Lee et al., Wavelet Methods for Inverting the Radon Transform with Noisy Data, IEEE Transactions on Image Processing, (2001) vol. 10, No. 1, pp. 79-94 (16 pages) (https://www.math.purdue.edu/~lucier/692/tomography.pdf).
Kutyniok et al., ShearLab 3D: Faithful Digital Shearlet Transforms based on Compactly Supported Shearlets, (2014) (39 pages) (Cornell University Archive, arXiv No. 1402.5670v1).
R-Forge User's Manual, (2011), SVN Revision: 227, 10 pages.
Daubechies Ten Lectures of Wavelets, Springer-Verlag, (1992), from CBMS-NSF Regional Conference Series in Applied Mathematics Society for Industrial and Applied Mathematics 1990 (344 pages).
Lawton, Seven Aneurysms Tenets and Techniques for Clipping (2011) Section 1, Thieme Medical Publishers, New York, Section 1, (36 pages).
Wikipedia article entitled "Band-pass filter", <https://en.wikipedia.org/wiki/Band-pass_filter>, last edited on Feb. 25, 2020, accessed on Mar. 26, 2020 (4 pages).
YouTube video, "Eulerian Video Magnification" accessed online on Jun. 15, 2020 at: <https://www.youtube.com/watch?v=ONZcjs1Pjmk>, published May 23, 2012 (2 pages).
U.S. Appl. No. 62/824,582 Entitled Device and Method for Reconstructing Cardiac Frequency Phenomena in Angiographic Data, Filed on Mar. 27, 2019 (25 pages).
Chen, C., et al., "Optical coherence tomography based angiography [Invited]," Biomedical Optics Express, vol. 8, No. 2, p. 1056, Jan. 24, 2017 (27 pages).

(56) References Cited

OTHER PUBLICATIONS

Zhang et al., "Application of Wavelet Thresholding De-noising in DSA," International Symposium on Information Science and Engineering IEEE Computer Society, 2008, pp. 130-134.
Akram et al., "Blood Vessel Enhancement and Segmentation Using Wavelet Transform, International Conference on Digital Image Processing IEEE Computer Society," 2009, pp. 34-38.
Cao et al., "Joint Spatio-Temporal Registration and Microvasculature Segmentation of Retinal Angiogram Sequences," 33rd Annual International Conference of the IEEE EMBS, 2011, pp. 2618-2621.
Tsai et al., "Motion Estimation and Wavelet Transform in Angiogram Video Coding," IEEE, 1994, pp. 1121-1125.
Oh et al., "Reversible Wavelet Compression for Digital Angiograms," Proceedings of the 20th Annual International Conference of the IEEE Engineering in Medicine and Biology Society, 1998, vol. 20, No. 3, pp. 1442-1445.
Tache et al., "Enhanced Visualization of Cerebral Blood Vessels for X-ray Angiograms," IEEE International Conference on E-Health and Bioengineering, 2013, pp. 1-13.
Sun et al., "Morphological enhancement of vascular angiogram with multiscale detected by Gabor filters," Electronics Letters, 2008, vol. 44, No. 2, pp. 1-3.
Munteanu et al., "Wavelet-Based Lossless Compression of Coronary Angiographic Images," IEEE Transactions on Medical Imaging, 1999, vol. 18, No. 3, pp. 272-281.
Lin et al., "Extraction of Coronary Arterial Tree Using Cine X-Ray Angiograms," Biomedical Engineering—Applications, Basis & Communications, 2005, pp. 111-120.
Hohne et al., "Fourier Domain Techniques for Digital Angiography of the Heart," IEEE Transactions on Medical Imaging, 1984, vol. MI-3, No. 2, pp. 62-67.
Hohne et al., "Proceedings of SPIE: Digital Angiography of the Heart in the Frequency Domain," Medical Images and Icons IEEE, 1984, pp. 245-250.
Havla et al., "Validation of a method to differentiate arterial and venous vessels in CT perfusion data using linear combinations of quantitative time-density curve characteristics," Eur. Radiol., 2015, vol. 25, pp. 2937-2944.
Farge, M., "Wavelet Transforms and Their Applications to Turbulence," Annu. Rev. Fluid Mech., 1992, vol. 24, pp. 395-457.
Havla, et al., "Classification of arterial and venous cerebral vasculature based on wavelet postprocessing of CT perfusion data," Med. Phys. (2016) 43 (2), pp. 702-709.
Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (8 pages).
Ashmead, John, "Morlet Wavelets in Quantum Mechanics," Quanta, vol. 1, issue 1, Nov. 2012, pp. 58-70 (13 pages).
Baker et al., "Lucas-Kanade 20 Years On: A Unifying Framework," International Journal of Computer Vision 56(3), 221-255, 2004 (35 pages).
Balakrishnan et al., "VoxelMorph: A Learning Framework for Deformable Medical Image Registration," arXiv: 1809.05231 [cs.CV], Sep. 1, 2019 (16 pages).
Bao et al., "Depth-Aware Video Frame Interpolation," IEEE Conference on Computer Vision and Pattern Recognition, pp. 3703-3712, 2019 (10 pages).
Chen et al., "A Labeling-Free Approach to Supervising Deep Neural Networks for Retinal Blood Vessel Segmentation," Chongqing University, China, May 1, 2017 (10 pages).
Bao et al., https://github.com/baowenbo/DAIN, "DAIN (Depth-Aware Video Frame Interpolation)", IEEE Conference on Computer Vision and Pattern Recognition, Long Beach, CVPR 2019 (9 pages).
Dalca et al., "Unsupervised Learning of Probabilistic Diffeomorphic Registration for Images and Surfaces," Jul. 23, 2019 (18 pages).
Garyfallidis et al., "Dipy, a library for the analysis of diffusion MRI data, " Frontiers in Neuroinformatics, vol. 8, art. 8, Feb. 21, 2014 (17 pages).
DIPY—Diffusion Imaging In Python; https://dipy.org/; accessed Mar. 1, 2021 (8 pages).
Daubechies, Ingrid, "Ten Lectures on Wavelets," CBMS-NSF Regional Conference Series in Applied Mathematics, Sep. 1992 (342 pages).
Farneback, Gunnar, "Very High Accuracy Velocity Estimation using Orientation Tensors, Parametric Motion, and Simultaneous Segmentation of the Motion Field," Proceedings Eighth IEEE International Conference on Computer Vision, Jul. 2001 (7 pages).
Felsberg and Sommer, "The monogenic signal," IEEE Transactions on Signal Processing, (49), 12, 3136-3144, 2001 (10 pages).
Chapter 2: Multiscale Vessel Enhancement Filtering, pp. 7-16, adapted from: Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (10 pages).
Freeman and Adelson, "The Design and Use of Steerable Filters," IEEE Transactions on Pattern Analysis and Machine Intelligence, vol. 13, No. 9, pp. 891-906, Sep. 1991 (16 pages).
Gabor, D., "Theory of Communication," Sep. 24, 1945 (29 pages).
Goupillaud et al., "Cycle-Octave and Related Transforms in Seismic Signal Analysis," Geoexploration, 23, (1984/85), pp. 85-102 (18 pages).
Harris and Stephens, "A Combined Corner and Edge Detector," Alvey Vision Conference, pp. 147-151, 1988 (5 pages).
Horn and Schunck, "Determining Optical Flow," Artificial Intelligence 17, pp. 185-203, 1981 (19 pages).
Wolfram Research, "ImageDisplacements," Wolfram Language function, https://reference.wolfram.com/language/ref/ImageDisplacements.html, 2016 (5 pages).
Lucas and Kanade, "An Iterative Image Registration Technique with an Application to Stereo Vision," Proceedings DARPA Image Understanding Workshop, Apr. 1981, pp. 121-130 (10 pages).
Morlet et al., "Wave propogation and sampling theory—Part I: Complex signal and scattering in multilayered media," Geophysics, vol. 47, No. 2, Feb. 1982, pp. 203-221 (19 pages).
Shi and Tomasi, "Good Features to Track," IEEE Conference on Computer Vision and Pattern Recognition, Seattle, Jun. 1994 (8 pages).
Simoncelli and Farid, "Steerable Wedge Filters for Local Orientation Analysis," IEEE Transactions on Image Processing, 5(9): 1377-1382, 1996 (10 pages).
Unser and Van De Ville, "Wavelet Steerability and the Higher-Order Riesz Transform," IEEE Transactions on Image Processing, vol. 19, No. 3, Dec. 22, 2009 (17 pages).
Yin et al., "Reducing the X-ray radiation exposure frequency in cardio-angiography via deep-learning based video interpolation," Jun. 1, 2020 (6 pages).
UK Examination Report in corresponding UK Application No. GB2110189.4, issued Jul. 20, 2022, 2 pages.
Abdallah, Considerations in perioperative assessment of valproic acid coagulopathy, review article, Journal of Anesthesiology Clinical Pharmacology, Jan.-Mar. 2014, vol. 30, iss. 1, pp. 7-9.
D'Agnolo et al., Radon-Penrose transform for D-modules, Sep. 6, 1994, pp. 1-37.
Penkov, A Geometric Approach to the Linear Penrose Transform, Transactions of the American Mathematical Society, Aug. 1985, vol. 290, No. 2, pp. 555-575.
Wolfram, Statistical mechanics of cellular automata, The American Physical Society, Reviews of Modern Physics, vol. 55, No. 3, Jul. 1983, pp. 601-644.
Sturm et al., New Brain Tumor Entities Emerge from Molecular Classification of CNS-PNETs, Cell, Feb. 25, 2016, vol. 164, iss. 5, pp. 1060-1072.
Liebling et al., Wavelet-based Synchronization of Nongated Confocal Microscopy Data for 4D Imaging of the Embryonic Heart, Proceedings of SPIE 5914, Wavelets XI, 2005, vol. 591409, 6 pages.
Ehrenreich et al., New developments in the understanding of cerebral vasoregulation and vasospasm: the endothelin-nitric oxide network, CME Credit, Cleveland Clinic Journal of Medicine, Mar.-Apr. 1995, vol. 62, No. 2, pp. 105-116.

(56) References Cited

OTHER PUBLICATIONS

Vagharshakyan et al., Light Field Reconstruction Using Shearlet Transform, Sep. 29, 2015, pp. 1-12 (Cornell University Archive, https://arxiv.org/abs/1509.08969, arXiv:1509.08969v1).

Daubechies, Orthonormal Bases of Compactly Supported Wavelets, Communications on Pure and Applied Mathematics, 1988, vol. XLI, pp. 909-996.

Mandelshtam, The Multidimensional Filter Diagonalization Method, Journal of Magnetic Resonance, 2000, vol. 144, pp. 343-356.

Insolera et al., Cortical neurogenesis in the absence of centrioles, Nat Neurosci, Nov. 2014, vol. 17, No. 11, pp. 1528-1536.

Kool et al., Molecular subgroups of medulloblastoma: an international meta-analysis of transcriptome, genetic aberrations, and clinical data of WNT, SHH, Group 3, and Group 4 medulloblastomas, 2012, Acta Neuropathol, vol. 123, pp. 473-484.

Kutyniok et al., Compactly Supported Shearlets, Approximation Theory XIII: San Antonio 2010, pp. 1-24.

Liner, An overview of wavelet transform concepts and applications, University of Houston, Feb. 26, 2010, pp. 1-17.

Liu et al., Motion Magnification, ACM Transactions on Graphics (TOG), Jul. 2005, vol. 24, iss. 3, pp. 519-526 (8 pages).

Lohani et al., Intrasacral meningocele in the pediatric population, J Neurosurg Pediatrics, Jun. 2013, vol. 11, pp. 615-622.

Long et al., Spatiotemporal wavelet analysis for functional MRI, NeuroImage, 2004, vol. 23, pp. 500-516.

Maltz et al., Fixed gantry tomosynthesis system for radiation therapy image guidance based on a multiple source x-ray tube with carbon nanotube cathodes, Medical Physics, May 2009, vol. 36, No. 5, pp. 1624-1636.

Mandelshtam, FDM: the filter diagonalization method for data processing in NMR experiments, Progress in Nuclear Magnetic Resonance Spectroscopy, 2001, vol. 38, pp. 159-196.

Mourant et al., Hemoglobin parameters from diffuse reflectance data, Journal of Biomedical Optics, Mar. 2014, vol. 19, No. 3, pp. 037004-1-037004-9.

D'Ariano, How to Derive the Hilbert-Space Formulation of Quantum Mechanics From Purely Operational Axioms, 20 pages (presented at conference "On the Present Status of Quantum Mechanics" held on Sep. 7-9, 2005, Mali Losinj, Croatia) (Cornell University Archive, https://arxiv.org/abs/quant-ph/0603011, arXiv.quant-ph/0603011v1).

Mixter, Ventriculoscopy and Puncture of the Floor of the Third Ventricle, Boston M. & S. Journal, Mar. 1, 1923, vol. 188, No. 9, pp. 277-278.

Moussa et al., Efficacy of postoperative antibiotic injection in and around ventriculoperitoneal shunt in reduction of shunt infection: A randomized controlled trial, Clinical Neurology and Neurosurgery, 2016, vol. 143, pp. 144-149.

Monici, Cell and tissue autofluorescence research and diagnostic applications, Biotechnology Annual Review, 2005, vol. 11, pp. 227-256.

Drexler et al., In vivo ultrahigh-resolution optical coherence tomography, Optics Letters, Sep. 1, 1999, vol. 24, No. 17, pp. 1221-1223.

Rees et al., Role of endothelium-derived nitric oxide in the regulation of blood pressure, Proc. Natl. Acad. Sci. USA, 1989, vol. 86, pp. 3375-3378.

Rodino et al., The Gabor Wave Front Set (2013) (Cornell University Archive, https://arxiv.org/abs/1207.5628, arXiv: 1207.5628v2), pp. 1-29.

Schaer et al., Haptoglobin Preserves Vascular Nitric Oxide Signaling during Hemolysis, American Journal of Respiratory and Critical Care Medicine, May 15, 2016, vol. 193, iss. 10, pp. 1111-1122.

Shumacher, Analog clock and watch reader, 2015, pp. 1-10 (https://www.cs.bgu.ac.il/~ben-shahar/Teaching/Computational-Vision/StudentProjects/ICBV151/ICBV-2015-1-ChemiShumacher/Report.pdf).

Tudor et al., Endoscopic third ventriculostomy (ETV) for idiopathic normal pressure hydrocephalus (iNPH) (Review), Cochran Collection, Cochrane Database of Systematic Reviews, 2015, iss. 7, pp. 1-23.

Khandelwal et al., Age-dependent increase in green autofluorescence of blood erythrocytes, J. Biosci. Sep. 2007, vol. 32, No. 6, pp. 1139-1145.

Wadhwa et al., Phase-Based Video Motion Processing, MIT Computer Science and Artificial Intelligence Lab, ACM Transactions on Graphics, Jul. 2013, vol. 32, No. 4, article 80, pp. 80:1-80:9.

Yang et al., Improved phase-resolved optical Doppler tomography using the Kasai velocity estimator and histogram segmentation, Optics Communications, Jul. 15, 2002, vol. 208, pp. 209-214.

Zhang et al., Orthogonal Complex Filter Banks and Wavelets: Some Properties and Design, IEEE Transactions on Signal Processing, Apr. 1999, vol. 47, No. 4, pp. 1039-1048.

Aaslid et al., Cerebral Autoregulation Dynamics in Humans, Stroke, 1989, vol. 20, pp. 45-52.

Adams et al., Symptomatic Occult Hydrocephalus with "Normal" Cerebrospinal-Fluid Pressure, A Treatable Syndrome, The New England Journal of Medicine, Jul. 15, 1965, vol. 273, No. 3, pp. 117-126.

Barina, Gabor Wavelets in Image Processing, Feb. 10, 2016, 6 pages (Cornell University Archive, https://arxiv.org/pdf/1602.03308.pdf, arXiv:1602.03308v1).

Bernardes et al., Digital Ocular Fundus Imaging: A Review, Ophthalmologica, 2011, vol. 226, pp. 161-181.

Bernardino et al., A Real-Time Gabor Primal Sketch for Visual Attention, Second Iberian Conference on Pattern Recognition and Image Analysis, 2005, 8 pages (http://vislab.isr.ist.utl.pt/publications/05-ibpria-alex.pdf).

Guo et al., Wavelets with composite dilations and their MRA properties, Applied and Computational Harmonic Analysis, 2006, vol. 20, pp. 202-236.

Goh et al., Subependymal giant cell tumors in tuberous sclerosis complex, Neurology, Oct. 2004, vol. 63, pp. 1457-1461.

Bo et al., Symbolic Representations in Motor Sequence Learning, Neuroimage, 2011, vol. 54, No. 1, pp. 417-426.

Bodranghien et al., Consensus Paper: Revisiting the Symptoms and Signs of Cerebellar Syndrome, Cerebellum, Jun. 2016, vol. 15, No. 3, pp. 369-391 (published online Jun. 2015) (23 pages).

Borsdorf et al., Separate CT-Reconstructions for 3D Wavelet Based Noise Reduction Using Correlation Analysis, 2007, IEEE Nuclear Science Symposium Conference Record, pp. 2633-2638.

Brouder et al., A Smooth Introduction to the Wavefront Set, Apr. 7, 2014, pp. 1-29 (Cornell University Archive, https://arxiv.org/pdf/1404.1778.pdf, arXiv:1404.1778v1).

Burt et al., The Laplacian Pyramid as a Compact Image Code, IEEE Transactions on Communications, Apr. 1983, vol. COM-31, No. 4, pp. 532-540.

Medda et al., A wavelet clustering technique for the identification of functionally connected regions in the rat brain using resting state fMRI, IEEE Statistical Signal Processing Workshop (SSP), Aug. 2012, pp. 424-427.

Mizuno-Matsumoto et al., Wavelet-crosscorrelation analysis: Non-stationary analysis of neurophysiological signals, Brain Topography, 2005, vol. 17, No. 4, pp. 237-252.

Morlet et al, Wave propagation and sampling theory—part I: Complex signal and scattering in multilayered media, Geophysics, Feb. 1982, vol. 47, No. 2, pp. 203-221.

Najmi et al., The continuous wavelet transform and variable resolution time-frequency analysis, Johns Hopkins Apl Technical Digest, 1997, vol. 18, No. 1, pp. 134-140.

Schultze-Kraft et al., Exploiting the potential of three dimensional spatial wavelet analysis to explore nesting of temporal oscillations and spatial variance in simulateous EEG-fMRI data, Progress in Biophysics and Molecular Biology, Mar. 2011, vol. 105(1-2), pp. 67-79.

Serroukh, Wavelet coefficients cross-correlation analysis of times series, Electronic Journal of Applied Statistical Analysis, 2012, vol. 5, iss. 2, pp. 289-296.

Shannon, Communication in the Presence of Noise, Proceedings of the IEEE, Feb. 1998, vol. 86, iss. 2, pp. 447-457.

Hardesty et al., Safety, efficacy, and cost of intraoperative indocyanine green angiography compared to intraoperative catheter angiography in cerebral aneurysm surgery, Journal of clinical neuroscience, Apr. 2014, pp. 1-6.

(56) References Cited

OTHER PUBLICATIONS

Hyvarinen et al., Indocyanine green fluorescence angiography, Acta Ophthalmologica, Aug. 1980, vol. 58(4), pp. 528-538.
Aaslid et al., Noninvasive transcranial doppler ultrasound recording of flow velocity in basal cerebral arteries, J Neurosurg, 1982, vol. 57(6), pp. 769-774.
Vo et al., Vonn distribution of relative phase for statistical image modeling in complex wavelet domain, Signal Processing, 2011, vol. 91(1), pp. 114-125.
Abramovich et al., Wavelet Analysis and Its Statistical Applications, Journal of the Royal Statistical Society Series D (The Statistician), 2000, vol. 49(1), pp. 1-29.
Kim et al., Cine MR CSF flow study in hydrocephalus: what are the valuable parameters? Acta neurochirurgica Supplement, 1998, vol. 71(6), pp. 343-346.
Kulkarni et al., Endoscopic third ventriculostomy in the treatment of childhood hydrocephalus, The Journal of Pediatrics, Aug. 2009, vol. 155, No. 2, pp. 254-259.
Meairs et al., Ultrasound, microbubbles and the blood-brain barrier, Progress in Biophysics & Molecular Biology, Apr. 2007, vol. 93(1-3), pp. 354-362.
Saikali et al., A three-dimensional digital segmented and deformable brain atlas of the domestic pig, Journal of Neuroscience Methods, Sep. 2010, vol. 192(1), pp. 102-109.
Wilson, Monro-Kellie 2.0: The dynamic vascular and venous pathophysiological components of intracranial pressure, Journal of Cerebral Blood Flow & Metabolism, May 2016, vol. 36(8), pp. 1338-1350.
Bernstein et al., Handbook of MRI Pulse Sequences, Elsevier Academic Press, 2004, pp. 443-454.
Kim et al., Phase-shift between arterial flow and ICP pulse during infusion test, Acta Neurochirurgica, Feb. 3, 2015, vol. 157(4), pp. 633-638.
Kawoos et al., Advances in Intracranial Pressure Monitoring and Its Significance in Managing Traumatic Brain Injury, International Journal of Molecular Sciences, 2015, vol. 16 (12), pp. 28979-28997.
Gabor, Theory of communication. Part 2: The analysis of hearing, Journal of the Institution of Electrical Engineers—Part III: Radio and Communication Engineering, 1946, vol. 93(26), pp. 442-445.
Goriely et al., Mechanics of the brain: perspectives, challenges, and opportunities, Biomechanics and modeling in mechanobiology, Feb. 26, 2015, vol. 14(5), pp. 931-965.
Helbok et al., Intracranial Pressure and Cerebral Perfusion Pressure Monitoring in Non-TBI Patients: Special Considerations, Neurocritical Care, 2014, vol. 21(S2), pp. S85-S94 (published online, Sep. 11, 2014, 10 pages).
Balestreri et al., Intracranial hypertension: what additional information can be derived from ICP waveform after head injury?, Acta Neurochirurgica (wien), 2004, vol. 146(2), pp. 131-141.
Carrera et al., What Shapes Pulse Amplitude of Intracranial Pressure?, Journal of Neurotrauma, Feb. 2010, vol. 27(2), pp. 317-324.
Bangare et al., Reviewing Otsu's method for image thresholding, International Journal of Applied Engineering Research, 2015, vol. 10, No. 9, pp. 21777-21783.
Bhadelia et al., Analysis of cerebrospinal fluid flow waveforms with gated phase-contrast MR velocity measurements, American Journal of Neuroradiology, Feb. 1995, vol. 16(2), pp. 389-400.
Bonnefous et al., Quantification of arterial flow using digital subtraction angiography, Medical Physics, Oct. 2012, vol. 39, iss. 10, pp. 6264-6275.
Chang et al., Emerging techniques for evaluation of the hemodynamics of intracranial vascular pathology, The Neuroradiology Journal, Feb. 2015, vol. 28(1), pp. 19-27.
Dawkins et al., Complications of cerebral angiography: A prospective analysis of 2,924 consecutive procedures, Neuroradiology, Aug. 2007, vol. 49, iss. 9, pp. 753-759.
Torrence et al., A Practical Guide to Wavelet Analysis, Bulletin of the American Meteorological Society, Jan. 1998, vol. 79, iss. 1, pp. 61-78.
Zou et al., Increased Phase Synchronization between Intracranial Pressure and Arterial Blood Pressure during Elevated Intracranial Pressure in Dogs, Proceedings of the 2005 IEEE, Engineering in Medicine and Biology 27th Annual Conference, Shanghai, China, Sep. 1-4, 2005, pp. 315-318.
Unekawa et al., RBC velocities in single capillaries of mouse and rat brains are the same, despite 10-fold difference in body size, Brain Research, 2010, vol. 1320, pp. 69-73.
Grinsted et al., Application of the cross wavelet transform and wavelet coherence to geophysical time series, Nonlinear Processes in Geophysics, 2004, vol. 11, pp. 561-566.
Grist et al., Time-Resolved Angiography: Past, Present, and Future, Journal of Magnetic Resonance Imaging, 2012, vol. 36(6), pp. 1273-1286.
Jiang et al., Computational Fluid Dynamics Simulations of Intracranial Aneurysms at Varying Heart Rates: A "Patient-Specific" Study, Journal of Biomechanical Engineering, Sep. 2009, vol. 131(9), pp. 09100-1-09100-11.
Kachelriess et al., ECG-correlated image reconstruction from subsecond multi-slice spiral CT scans of the heart, Medical Physics, 2000, vol. 27(12), pp. 1881-1902.
Kirk et al., Phase-only complex-valued spatial filter, Journal of the Optical Society of America, Aug. 1971, vol. 61, iss. 8, pp. 1023-1028.
Latka et al., Phase dynamics in cerebral autoregulation, American journal of physiology, heart and circulatory physiology, 2005, vol. 289(5), pp. H2272-H2279.
Shpilfoygel et al., X-ray videodensitometric methods for blood flow and velocity measurement: A critical review of literature, Medical Physics, Sep. 2000, vol. 27, iss. 9, pp. 2008-2023.
Mistretta, Sub-Nyquist acquisition and constrained reconstruction in time resolved angiography, Medical Physics, 2011, vol. 38, iss. 6, pp. 2975-2985.
Peng et al., Wavelet phase synchronization analysis of cerebral blood flow autoregulation, IEEE Transactions on Biomedical Engineering, Apr. 2010, vol. 57, No. 4, pp. 960-968.
Pereira et al., A DSA-based method using contrast motion estimation for the assessment of the intra-aneurysmal low changes induced by flow-diverter stents, American Journal of Neuroradiology, Apr. 2013, vol. 34(4), pp. 808-815.
Wendy Bottinor, MD, et al. "Adverse Reactions to Iodinated Contrast Media", International Journal of Angiology, vol. 22, No. Mar. 2013, Aug. 16, 2013, 5 pages.
Yumi Yanaga, et al., "Contrast Material Injection Protocol With the Dose Adjusted to the Body Surface Area for MDCT Aortography", AJR:194, Apr. 2010, 6 pages.
Keika Ose, et al., "'Gadolinium' as an Alternative to Iodinated Contrast Media for X-Ray Angiography in Patients With Severe Allergy", Circ J 2005; 69: 507-509, Circulation Journal, vol. 69, Apr. 2005, 3 pages.
H. Kälsch, M.D., et al., "Gadolinium-Based Coronary Angiography in Patients with Contraindication for Iodinated X-Ray Contrast Medium: A Word of Caution", Journal of Interventional Cardiology, vol. 21, No. 2, 2008, 9 pages.
Rohit S. Loomba, MD, et al., "Comparison of Contrast Volume, Radiation Dose, Fluoroscopy Time, and Procedure Time in Previously Published Studies of Rotational Versus Conventional Coronary Angiography", The American Journal of Cardiology, Am J Cardiol 2015;116:43e49, 7 pages.
Hrvoje Lusic, et al., "X-Ray Computed Tomography Contrast Agents", Chem Rev. Mar. 13, 2013; 113(3), NIH-PA Author Manuscript, 64 pages.
Kreton Mavromatis, MD, "The Imperative of Reducing Contrast Dose in Percutaneous Coronary Intervention", Editorial Comment, JACC: Cardiovascular Interventions, vol. 7, No. 11, 2014, 3 pages.
Sun Y. Lee, et al., "A Review: Radiographic Iodinated Contrast Media-Induced Thyroid Dysfunction", J Clin Endocrinol Metab., Feb. 2015; 100(2): 376-383, Published online Nov. 6, 2014, 15 pages.
Zhao et al., Ultrasound Contrast Imaging Based on a Novel Algorithm Combined Pulse Inversion with Wavelet Transform, Ultrasound in Medicine & Biology, 2011, vol. 37, No. 8, pp. 1292-1305.

(56) References Cited

OTHER PUBLICATIONS

Faubel et al., Cilia-based flow network in the brain ventricles, Neurophysiology, Jul. 8, 2016, vol. 353, iss. 6295, pp. 176-178.
Marshall et al., Cilia orientation and the fluid mechanics of development, Current Opinion in Cell Biology, 2008, vol. 20(1), pp. 48-52.
Ohata et al., Mechanosensory Genes Pkd1 and Pkd2 Contribute to the Planar Polarization of Brain Ventricular Epithelium, The Journal of Neuroscience, Aug. 5, 2015, vol. 35(31), pp. 11153-11168.
Jalalvand et al., Ciliated neurons lining the central canal sense both fluid movement and pH through ASIC3, Nature Communications, Jan. 8, 2016, pp. 1-12.
Wagshul et al., Resonant and notch behavior in intracranial pressure dynamics, J Neurosurgery Pediatrics, May 2009, vol. 3(5), pp. 354-364.
Park et al., Alterations of pulsation absorber characteristics in experimental hydrocephalus, J Neurosurg Pediatrics, Aug. 2010, vol. 6(2), pp. 159-170.
Sarode et al., Video Motion Magnification Using Spatio-Temporal Algorithm, International Journal of Computer Applications (0975-8887), Jun. 2014, vol. 96, No. 9, pp. 9-13.
Zhao et al., Phase-Resolved Optical Coherence Tomography and Optical Doppler Tomography for Imaging Blood Flow in Human Skin with Fast Scanning Speed and High Velocity Sensitivity, Optics Letters, Jan. 15, 2000, vol. 25, iss. 2, pp. 114-116.
Yazdanfar et al., High Resolution Imaging of In vivo Cardiac Dynamics Using color Doppler Optical Coherence Tomography, Optics Express, Dec. 22, 1997, vol. 1, No. 13, pp. 424-431.
Wu et al., Eulerian Video Magnification for Revealing Subtle Changes in the World, ACM Transactions on Graphics, Jul. 1, 2012, vol. 31, iss. 4, pp. 1-8.
Wang et al., Phase-Sensitive Optical Coherence Elastography for Mapping Tissue Microstains in Real Time, Applied Physics Letter, 2007, vol. 90, pp. 164105-1-164105-3.
Robles et al., Assessing Hemoglobin Concentration Using Spectroscopic Optical Coherence Tomography for Feasibility of Tissue Diagnostics, Biomedical Optics Express, Aug. 2, 2010, vol. 1, No. 1, pp. 310-317.
Lahiri et al., Medical Applications of Infrared Thermography: A Review, Infrared Physics & Technology, 2012, vol. 55, pp. 221-235.
Mourant et al., Hemoglobin Parameters from Diffuse Reflectance Data, Journal of Biomedical Optics, Mar. 2014, vol. 19, iss. 3, pp. 037004-1-037004-9.
Chen et al., Noninvasive Imaging of in vivo blood flow velocity using optical Doppler tomography, Optics Letters, Jul. 15, 1997, vol. 22, No. 14, pp. 1119-1121.
Izatt et al., In vivo bidirectional color Doppler flow imaging of picoliter blood volumes using optical coherence tomography, Optics Letters, Sep. 15, 1997, vol. 22, No. 18, pp. 1439-1441.
Drexler, Ultrahigh-Resolution Optical Coherence Tomography, Journal of Biomedical Optics, Jan./Feb. 2004, vol. 9, iss. 1, pp. 47-74.
Devor et al., Frontiers in optical imaging of cerebral blood flow and metabolism, Journal of Cerebral Blood Flow & Metabolism, 2012, vol. 32, pp. 1259-1276.
Chen et al., Optical Doppler Tomography, IEEE Journal on Selected Topics in Quantum Electronics, Jul. 1, 1999, vol. 5, No. 4, pp. 1134-1142.
Bachmann et al., Fluorescence Spectroscopy of Biological Tissues—A Review, Applied Spectroscopy Reviews, 2006, vol. 41, pp. 575-590.
Desmettre et al., Fluorescence Properties and Metabolic Features of Indocyanine Green (ICG) as Related to Angiography, Survey of Ophthalmology, Jul.-Aug. 2000, vol. 45, No. 1, pp. 15-27.
Martin et al., Hydrodynamic and longitudinal impedance analysis of cerebrospinal fluid dynamics at the craniovertebral junction in type I Chiari malformation, PloS One, Oct. 2013, vol. 8, iss. 10, pp. 1-9.
Bracewell, R. N., "Two-Dimensional Imaging", Prentice Hall, chapters 4-7, 12, and 15, 1995 (206 pages).
Des Plantes, "Eine Neue Methode Zur Differenzierung in der Rontgenographie (Planigraphies)," Acta Radiologica, 13:2, 182-192, 1932 (16 pages).
Tuy, H. K., "An Inversion Formula for Cone-Beam Reconstruction," SIAM Journal on Applied Mathematics, 43(3):546-552, 1983 (7 pages).
Martin J. Murphy, "Tracking Moving Organs in Real Time", Seminars in Radiation Oncology, vol. 14, No. 1, Jan. 2004, pp. 91-100.
Notification of Reasons for Refusal with English translation in Japanese Patent Application No. 2021-541315, issued Aug. 9, 2022, 8 pages.
Examination Report in Canadian Patent Application No. 3,127,005, issued Sep. 28, 2022, 9 pages.
Notice on the First Office Action with English translation in Chinese Patent Application No. 202080013191.9, issued Aug. 30, 2022, 28 pages.
Extended Search Report in EP Application No. 20752968.6, issued Sep. 15, 2022, 6 pages.
KR Notice of Preliminary Rejection in corresponding KR Application No. 10-2021-7025010, issued Jun. 12, 2022, 16 pages.
Office Action in corresponding CN Application No. 202080013191.9, issued Jun. 21, 2023 (13 pages).
Office Action in corresponding GB Application No. 2110189.4, issued Mar. 17, 2023 (4 pages).
Office Action in corresponding KR Application No. 10-2021-7025010, issued Dec. 27, 2023 (6 pages).
International Preliminary Report on Patentability for PCT/US2020/017037, issued Aug. 10, 2021 (8 pages).

* cited by examiner

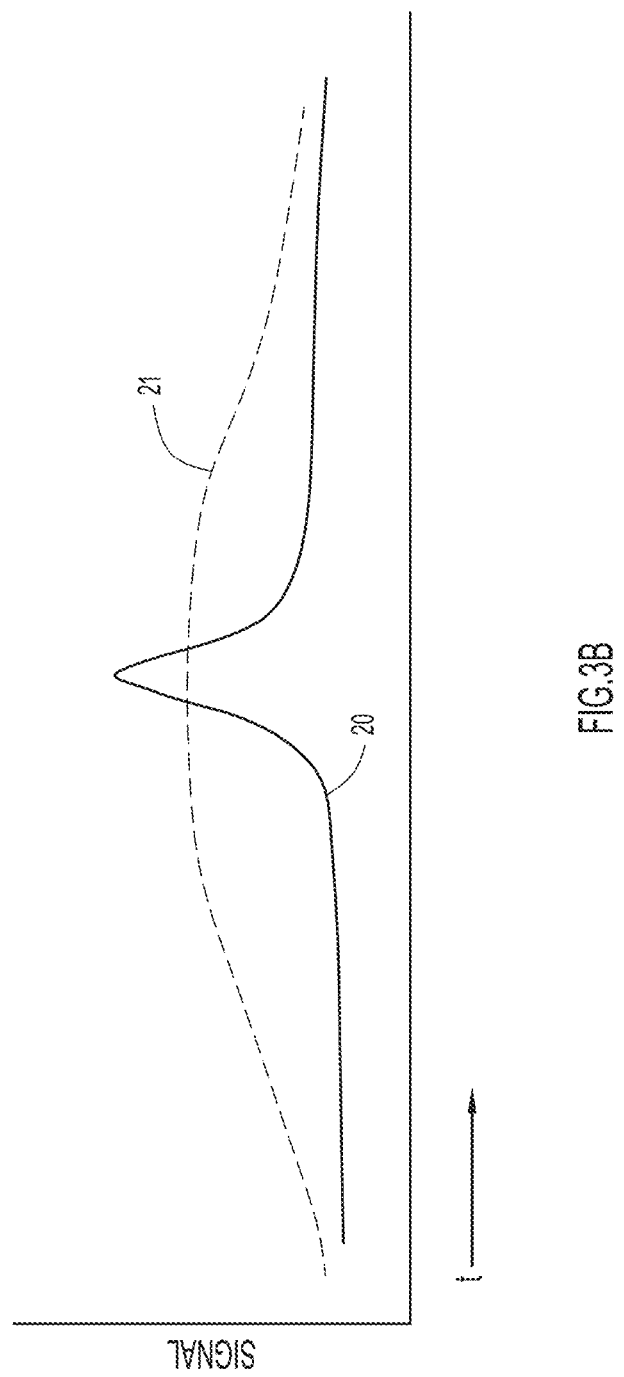

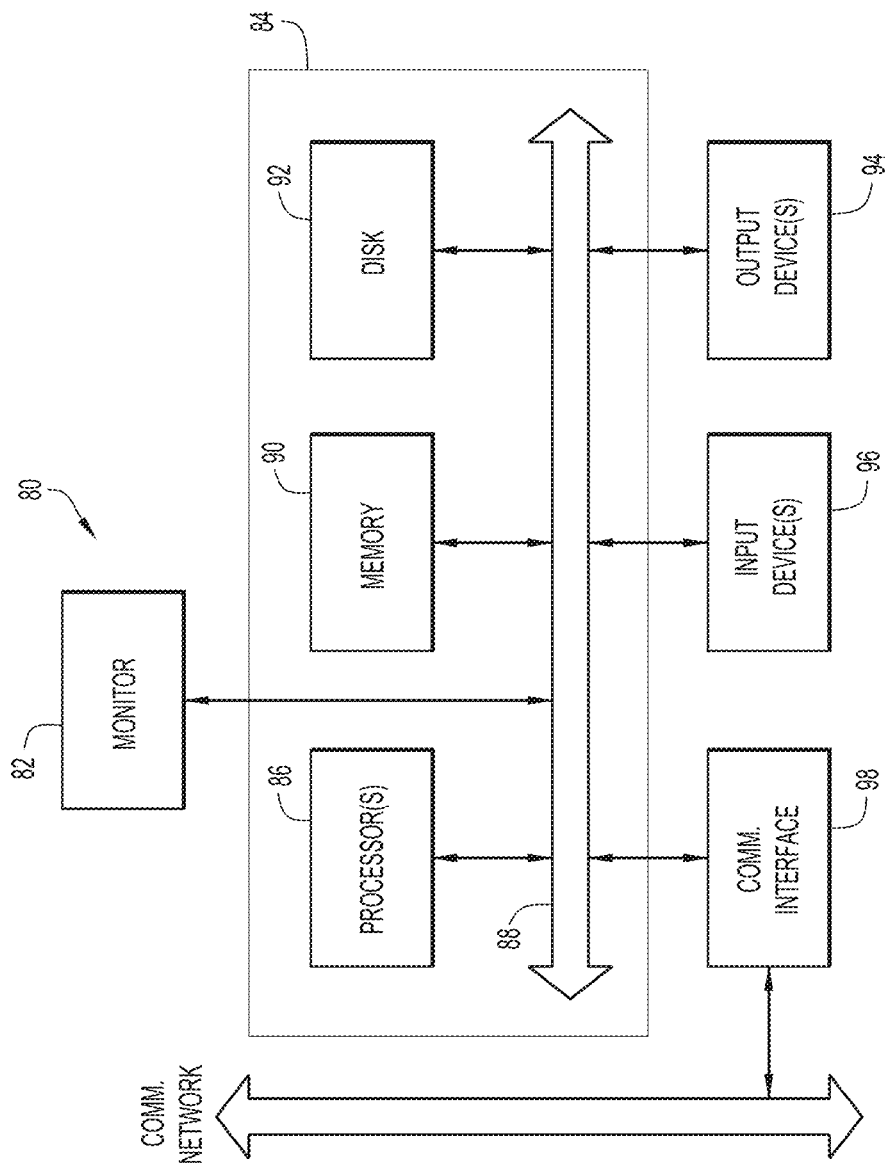

METHODS FOR ANGIOGRAPHY

CROSS-REFERENCE TO RELATED APPLICATIONS

This application claims priority to U.S. Provisional Application No. 62/801,780, filed Feb. 6, 2019, the contents of which are hereby incorporated by reference in their entirety.

FIELD OF THE INVENTION

Improved methods for angiography are provided. Specifically, methods of obtaining angiographic data are provided that permit use of greatly reduced doses of contrast agent and/or x-ray dosage, while maintaining, or improving the signal to noise ratio of the angiogram.

BACKGROUND OF THE INVENTION

In a conventional catheter angiogram, a catheter is placed into an artery and the catheter tip is advanced into the arterial region of interest. A chemical contrast agent is injected and the passage of the contrast to the vascular bed is fluoroscopically imaged and recorded. The contrast agent is opaque to the x-ray, causing a pattern of opacification to appear on the imaging x-ray detector in a sequence of angiographic image frames. Vascular anatomy may be characterized by the opacification pattern in an image in relation to normative patterns of anatomy as recorded in textbooks and other resources. A signal to noise ratio may be measured by comparing (a) the degree of opacification of a contrast-containing vessel upon projection onto the x-ray detector and (b) background, where the background is defined by regions without vascular anatomy containing chemical contrast agent and/or auto-fluorescence.

The anatomy is further characterized by the passage timing properties of the bolus of injected contrast agent. The chemical contrast agent passes through the arterial subsystem of circulation, the capillary subsystem, and then the venous subsystem, with overlap between these events. Differentiation between arterial and venous anatomy is interpreted by the timing of the image frame where opacified vascular anatomy appears.

To sharpen the contrast between the vascular tree and the non-vascular tissues sufficiently to obtain a diagnostically useful image, the quantity and concentration of the injected chemical vascular contrast agent may need to be high and the x-ray dose also may need to be high. Elevating the contrast dose and/or the x-ray dose increases the signal to noise ratio in the produced angiographic images, but also increases the risk to the subject in several ways.

The injected chemical contrast agent has toxic side effects to kidneys and other internal organs, and therefore it often is necessary to lower the dose of contrast agent to reduce the risk of these toxic side effects. This may produce unsatisfactory images with poor signal to noise ratios which, in turn, may lead to incomplete angiographic studies with inadequately imaged vascular anatomy. Use of an elevated chemical contrast dose may lead to injury to those organs vulnerable to chemical contrast side effects. It may also compel the advancement of the injecting catheter further into the arterial tree so that the injected contrast remains concentrated within the anatomic region of interest. The need to advance the injecting catheter further elevates the risk of complications caused by the catheter injuring ever smaller vessels distal in the vascular tree.

SUMMARY OF THE INVENTION

Methods of imaging a mammalian host are provided, in which an imaging effective amount of a contrast agent is administered to the host and angiographic data of the host is obtained, where the angiographic data is processed to generate a diagnostically useful image containing a spatiotemporal reconstruction of cardiac frequency angiographic phenomena from the angiographic data, where the cardiac frequency angiographic phenomena is a periodic, physiologically coherent signal with a corresponding cardiac frequency magnitude and a cardiac frequency phase; where the imaging effective amount of the contrast agent is significantly less than the amount required to produce a diagnostically useful image in the absence of extracting the spatiotemporal reconstruction of cardiac frequency angiographic phenomena; and/or where the signal to noise ratio is significantly improved compared to the signal to noise ratio obtained in the absence of extracting the spatiotemporal reconstruction of cardiac frequency angiographic phenomena.

Methods also are provided for reducing the toxicity of imaging a mammalian host, in which an imaging effective amount of a contrast agent is administered to the host and angiographic data of the host is obtained, where the angiographic data is processed to generate a diagnostically useful image containing a spatiotemporal reconstruction of cardiac frequency angiographic phenomena from the angiographic data, where the cardiac frequency angiographic phenomena is a periodic, physiologically coherent signal with a corresponding cardiac frequency magnitude and a cardiac frequency phase; where the effective amount of the contrast agent is significantly less than the amount required to produce a diagnostically useful image in the absence of extracting the spatiotemporal reconstruction of cardiac frequency angiographic phenomena.

In addition, methods are provided for reducing or preventing contrast nephropathy during angiographic imaging of a mammalian host, in which an imaging effective amount of a contrast agent is administered to the host and angiographic data of the host is obtained, where the angiographic data is processed to generate a diagnostically useful image containing a spatiotemporal reconstruction of cardiac frequency angiographic phenomena from the angiographic data, where the cardiac frequency angiographic phenomena is a periodic, physiologically coherent signal with a corresponding cardiac frequency magnitude and a cardiac frequency phase; where the imaging effective amount of the contrast agent is significantly less than the amount required to produce a diagnostically useful image in the absence of extracting the spatiotemporal reconstruction of cardiac frequency angiographic phenomena.

In each of these methods, the imaging may be x-ray imaging. The contrast agent may be an iodine-containing imaging agent, for example, a non-ionic iodine-containing imaging agent, or the contrast agent may be a gadolinium-containing imaging agent.

The imaging effective amount of the contrast agent is at least 25%, at least 50%, or at least 75%, less than the amount required to produce a diagnostically useful image in the absence of extracting the spatiotemporal reconstruction of cardiac frequency angiographic phenomena.

The image may be, for example, an image of; (a) part or all of the heart of the subject, (b) part or all of a kidney of the subject; part or all of the cranium of the subject; and/or part or all of the brain, neck, heart, chest, abdomen, pelvis, legs, feet, arms or hands of the subject.

Also provided are methods of reducing the toxicity of x-ray imaging in a mammalian host, in which an imaging effective amount of a contrast agent is administered to the host and x-ray angiographic data of the host is obtained at faster than cardiac frequency of the host, where the angiographic data is processed to generate a diagnostically useful image containing a spatiotemporal reconstruction of cardiac frequency angiographic phenomena from the angiographic data, where the cardiac frequency angiographic phenomena is a periodic, physiologically coherent signal with a corresponding cardiac frequency magnitude and a cardiac frequency phase; and where the dose of the x-ray required to obtain a diagnostically useful image is significantly less than the amount required to produce a diagnostically useful image in the absence of extracting the spatiotemporal reconstruction of cardiac frequency angiographic phenomena. In these methods the x-ray dosage required to obtain a diagnostically useful image may be at least 25%, at least 50%, or at least 75% less than the amount required to produce a diagnostically useful image in the absence of extracting cardiac frequency magnitude and phase for plurality of pixels.

BRIEF DESCRIPTION OF THE DRAWINGS

FIGS. 3A and 3B illustrate an angiographic catheter that is navigated further into a vascular tree to obtain an angiogram with a sharper contrast travel profile with a lower dose of contrast and a corresponding cardiac signal profile.

FIG. 5 is a block diagram of a computer system or information processing device that may be used with embodiments of the invention.

DETAILED DESCRIPTION

Figure 1:
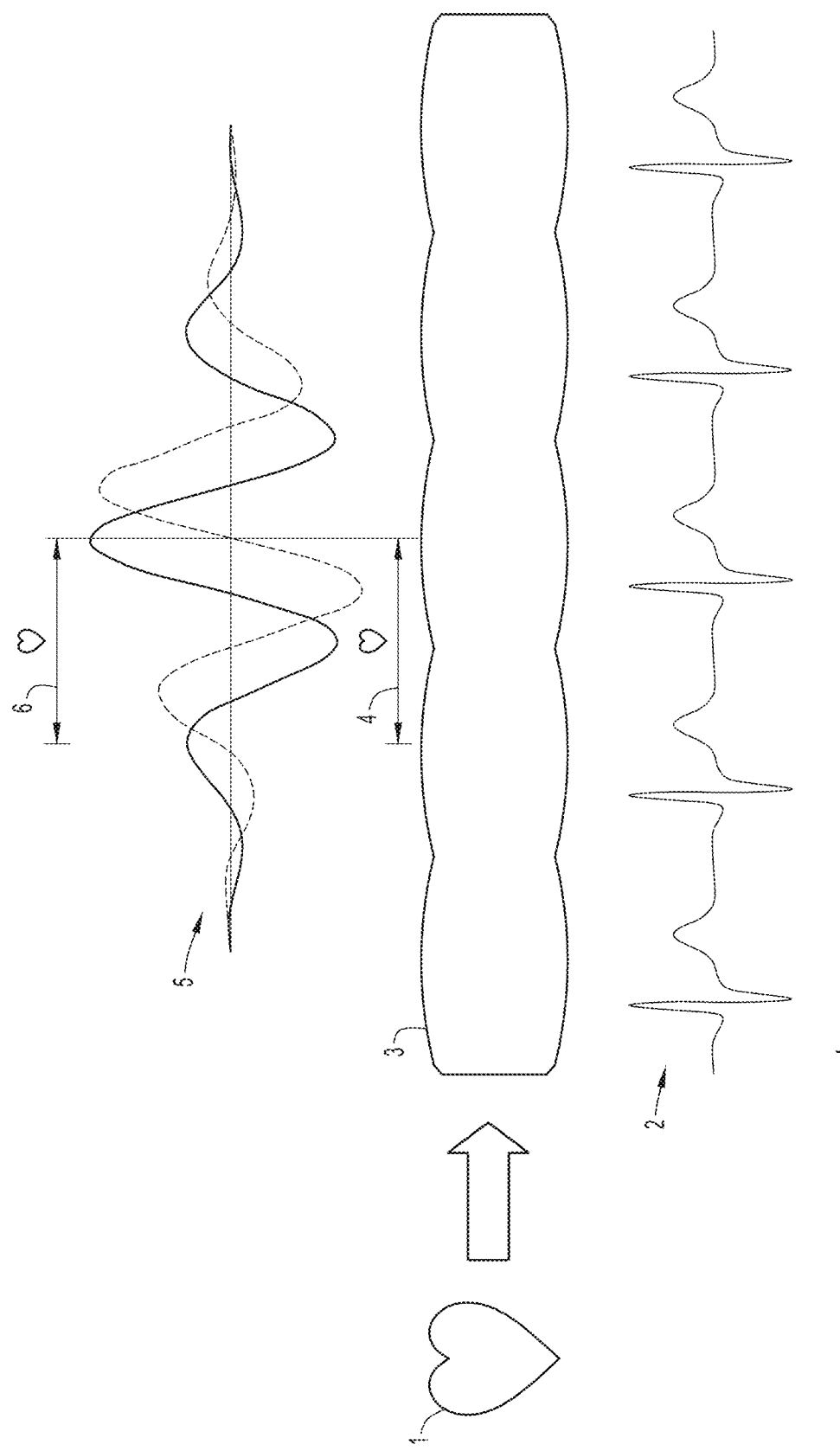
FIG. 1 illustrates the enabling discovery of a method to extract and represent cardiac frequency magnitude and phase, based on a spatiotemporal reconstruction, e.g., using wavelets, in an angiogram that is exploited to offer a process to increase the angiographic informational yield or net signal to noise ratio per pixel.

Compositions and methods are provided that permit angiographic images and information to be obtained while using lower intravascular contrast dose, lower x-ray dose, and/or less distance navigation of a catheter that injects the angiographic contrast into a vascular tree. The methods use data processing techniques, applied to an angiogram, to generate a spatiotemporal reconstruction, e.g., using wavelets, also referred to as a cardiac space angiogram. See U.S. Pat. No. 10,123,761, the contents of which are hereby incorporated by reference in their entirety. Present techniques exploit the organization of cardiac frequency phase, including coherence, and cardiac frequency from the cardiac space angiogram with regard to reducing x-ray exposure and/or contrast dosage, as well as positioning of the catheter, as described herein. The presence of angiographic coherence increases the net signal in the captured data, and the increase in net signal reduces or eliminates the need for conventional methods of increasing the signal such as increased contrast dose, increased x-ray dose, and further navigation of the injecting catheter. In addition, the coherence between the arterial and venous subsystems of circulation provides a way (other than by the travel timing of a contrast bolus) of providing angiographic contrast. This allows discrimination between arterial and venous angiographic information using a venous injection of contrast, which avoids the risk to the subject of invasion of the arterial system by an injection catheter.

The methods described herein allow reduction of the dose of the intravascular contrast agent used in an angiographic procedure and therefore reduces the risk of toxic side effects caused by the contrast agent in the patient. Most intravascular contrast chemical forms are nephrotoxic, and therefore improved methods that permit use of a lower dose of contrast agent are especially valuable in patients with renal disease, although the skilled artisan will recognize that lowering the dose of contrast agent is advantageous in all patients.

The methods described herein permit the x-ray dose received by a patient during angiography to be reduced, and thereby reduces the risk of harm to the patient from that x-ray radiation. Alternately, for the same total x-ray dose, the methods allow the acquisition of greater imaging information for the same total x-ray dose. Furthermore, angiography health care professionals have some of the highest exposure to x-ray radiation and, accordingly, reducing the x-ray dose has the secondary benefit of sparing incidental x-ray dosing to medical personnel.

Reducing the x-ray dose has the further advantage of reducing the equipment requirements to generate the extra dose and to capture it in an image, and to shield the local environment from the x-ray dose. Reducing the equipment footprint allows equal or greater angiographic imaging information to be obtained from a smaller hardware configuration that draws less electrical power and allows improvements in the field of portable angiography.

Obtaining a diagnostically useful angiographic image often requires advancing the injecting catheter further into the arterial tree so that the injected contrast remains concentrated within the anatomic region of interest. This increases the risk of complications caused by the catheter injuring ever smaller vessels distal in the vascular tree. Increasing the signal-to-noise ratio by exportation of angiographic coherence reduces the procedural risk to the patient by reducing the distance in the vascular tree to which a catheter needs to be advanced for study.

The methods described herein generate an increased signal to noise ratio in an angiographic study by exploiting the organized cardiac frequency magnitude and phase, from a spatiotemporal reconstruction, e.g., using wavelets, within the vascular tree. The methods further exploit the presence of coherence at cardiac frequency between the arterial and venous subsystems of circulation. This means that arteries in an angiogram generally pulse with shared phase, veins generally pulse with shared phase, and these phases do not overlap but instead generally maintain a relatively fixed difference. Exploiting coherence between the arterial and venous components of the circulation allows arterial anatomy to be distinguished from venous anatomy in an angiogram at lower contrast and x-ray doses using criteria other than the travel timing of an injected bolus of chemical contrast agent.

Furthermore, this coherence allows detection of altered patterns of circulation, such as the disruption or occlusion of an artery or of a vein. Such an injury alters the coherence relationship between the arterial and venous sides of a vascular bed, providing biomarkers for the disruption of the vascular tree.

Spatiotemporal Reconstructions of Cardiac Frequency Phenomena

Method for extracting vascular anatomy and physiology information are provided by analyzing the patterns of cardiac frequency magnitude, phase, and coherence in a spatiotemporal reconstruction of cardiac frequency phenomena extracted from an angiogram obtained at faster than cardiac frequency. The spatiotemporal reconstructions of cardiac frequency phenomena are described in detail in U.S. Pat. No. 10,123,761, the contents of which are hereby incorporated by reference in their entirety.

The term "cardiac space angiogram" as used herein refers to the totality of the product of a spatiotemporal reconstruction of cardiac frequency phenomena as described by the '761 patent. The cardiac space angiogram includes not only the spatiotemporal reconstructions of cardiac frequency phenomena as generated by a computer program, but also the angiogram that the computer program operates upon. Accordingly, the cardiac space angiogram includes all of the information of a conventional angiogram plus the additional information contained in the spatiotemporal reconstruction of the cardiac frequency phenomena. Advantageously, the method described by the '761 patent is applied in a computer program to generate a cardiac space angiogram, however the skilled artisan will recognize that other methods of reconstructing the spatiotemporal cardiac frequency activity may be used.

A cardiac space angiogram is based on angiographic images acquired at faster than cardiac rate, in compliance with the sampling theorem of Nyqvist, Kotelnikov, and Shannon, as known in the art. This method can resolve single vascular pulse waves, as distinguished from cardiac gated methods where one cardiac cycle is interpolated from many.

As described above, the signal at cardiac frequency in an angiogram is exploited to increase the sensitivity of angiographic imaging to arterial anatomy and to venous anatomy, allowing identification of altered and pathological patterns of circulation such as vessel occlusions and other blood flow states at lower x-ray doses and at lower intravascular contrast doses. Additionally, it allows the separation of arterial from venous anatomy without navigating and injecting a catheter into the distal arterial tree. The coherence at cardiac frequency among circulatory sub-systems may be exploited to allow the anatomic identification of arterial anatomy and venous anatomy at lower x-ray doses and at lower intravascular contrast doses.

In carrying out the methods described herein, the angiographic data are recorded using a digital detector device, such as those commercially available as part of scanning devices available from manufacturers such as Philips and Siemens. The digital data are then imported into a computer memory. After the import into computer memory of an angiogram (in the absence of motion alias), the spatiotemporal reconstruction of cardiac frequency angiographic phenomena may be obtained by the following steps:

the angiographic data consisting of n by m pixels by q frames data is imported into computer memory and reformatted with the processor in memory to give an n by m array of time signals each q samples long;

a complex valued wavelet transform is applied by the processor to each pixel-wise time signal, giving an n by m array of wavelet transforms;

the pixel-wise wavelet transforms are filtered for cardiac frequency by the processor. This is done by setting to zero all wavelet coefficients that do not correspond to cardiac wavelet scale (in the field of wavelets this term corresponds to the concept of cardiac frequency);

the pixel-wise wavelet transforms data are inverse wavelet transformed by the processor into time domain and reformatted in computer memory into q frames of n by m pixels. Each data element (voxel) in this three dimensional grid is a complex valued number;

each frame can be rendered as an image with a brightness hue color model to represent the complex datum in each pixel by the processor;

cardiac frequency magnitude is represented as brightness and phase as hue; and the q images may be rendered as motion cine by the processor or they may be stored as a video file format by the processor.

Any suitable transform, operable on complex numbers that retain time indexing after transformation into the frequency domain, and capable of extracting the spatiotemporal reconstruction of cardiac frequency angiographic phenomena is contemplated for use with the present techniques.

Contrast Agents

The methods described herein provide methods of greatly reducing the dose of contrast agent required to obtain a diagnostically useful angiogram. A "diagnostically useful" angiogram is one that provides the person reading the angiogram (such as a radiologist) with data of a quality sufficient to provide meaningful clinical information and/or to allow treatment decisions to be made. Although a reduction in dose of contrast agent is generally desirable for all subjects undergoing angiography, contrast nephropathy is particularly problematic for patients with impaired kidney function or who are otherwise renally vulnerable. See, generally, Mavromatis, "The Imperative of Reducing Contrast Dose in Percutaneous Coronary Intervention," *Cardiovascular Interventions* 7:1294-1296 (2014). Accordingly, such patients particularly benefit from using the instant methods to reduce or prevent contrast nephropathy during angiographic imaging.

The main type of contrast agent used in angiography is the family of iodinated contrast agents, which can be ionic or, advantageously, non-ionic iodinated contrast agents. Such agents are well known in the art and include: iohexol (Omnipaque™, GE Healthcare); iopromide (Ultravist™, Bayer Healthcare); iodixanol (Visipaque™, GE Healthcare); ioxaglate (Hexabrix™, Mallinckrodt Imaging); iothalamate (Cysto-Conray II™ Mallinckrodt Imaging); and iopamidol (Isovue™, Bracco Imaging). See also Lusic and Grinstaff, "X-Ray Computed Tomography Contrast Agents," *Chem Rev.* 13:1641-66 (2013). Other agents include gadolinium-based agents. See Ose et al., "'Gadolinium' as an Alternative to Iodinated Contrast Media for X-Ray Angiography in Patients With Severe Allergy," *Circ J.* 2005; 69:507-509 (2005).

The dosages for such contrast agents vary depending on the nature of the agent, the physical characteristics of the patient/subject, and the nature of the angiographic procedure. In general however, the contrast agent should improve the visualization of the target tissue by increasing the absolute CT attenuation difference between the target tissue and surrounding tissue and fluids by a factor of ≈2×. The imaging media should contain a high mol % of the x-ray attenuating atom per agent (molecule, macromolecule, or particle) in order to reduce the volume used and concentrations needed for imaging. Also, the tissue retention-time of the contrast agent should be sufficiently long for completion of a CT scan and scheduling the instrument time in the diagnostic setting (e.g., 2-4 h). Moreover, the contrast agent advantageously should: (a) localize or target the tissue of interest and possess favorable biodistribution and pharmacokinetic profiles; (b) be readily soluble or form stable suspensions at aqueous physiological conditions (appropriate pH and osmolality) with low viscosity; (c) be non-toxic; and (d) be cleared from the body in a reasonably short amount of time, usually within several hours (<24 h).

Even if a contrast agent meets these criteria, it is generally desirable to reduce the dosage used for imaging, and this is particularly the case for patients with reduced kidney function or who have an allergic or other adverse reaction to the agent. The methods described herein allow the use of a dose of contrast agent that is significantly less than the dosage that would otherwise be required to provide diagnostically useful imaging information. In this context of contrast agent dosage, a dose is significantly less if it less than 75%, less than 50%, less than 40%, less than 30%, less than 25%, less than 20%, less than 15%, less than 10%, less than 5% or less than 3% of the dose that would otherwise be required to produce a diagnostically useful angiogram.

X-Ray Dosage

The x-ray dosage required to generate a diagnostically useful image in an angiogram also varies depending on physical characteristics of the patient/subject and the nature of the angiographic procedure. Methods of calculating x-ray dosages are well known in the art. The ionizing nature of x-ray radiation means that it is always desirable to minimize the exposure of the subject (and medical staff associated with an angiography procedure) to x-rays as much as possible while still producing a useful visualization of the target tissue. In this context of x-ray dosage, an x-ray dose is significantly less if it less than 75%, less than 50%, less than 40%, less than 30%, less than 25%, less than 20%, less than 15%, less than 10%, less than 5% or less than 3% of the x-ray dose that would otherwise be required to produce a diagnostically useful angiogram.

Signal to Noise Ratio

The signal to noise ratio of an angiogram depends, inter alia, on both the dosage of the contrast agent, and the dose of the x-ray. The instant methods allow for a significant increase in the signal to noise ratio for a given dose of contrast agent and/or x-ray dosage. In the context of the instant methods, a significant increase or improvement of the signal to noise ratio is one that permits the dosage of either the contrast agent and/or the x-ray to be less than 75%, less than 50%, less than 40%, less than 30%, less than 25%, less than 20%, less than 15%, less than 10%, less than 5% or less than 3% of the dose that would otherwise be required to produce a diagnostically useful angiogram.

The arrangement in FIG. 1 provides a schematic that shows how the methods described herein provide increased signal to noise ratio compared to conventional angiography. In FIG. 1, a heart 1 sends blood to the body as a sequence of arterial stroke volumes. The work of the heart generates a cardiac signal. An example of this is the electrocardiogram 2. An artery 3 has contrast variation produced by the traveling arterial stroke volumes. The time between the arterial stroke volumes is the cardiac period 4, and is also the time between cardiac cycles in the electrocardiogram 2. A mother wavelet 5 function is created in a computer program with a wavelet cardiac scale 6 that matches the cardiac period 4 of the cardiac signal. Advantageously, the Gabor wavelet family is selected for mother wavelet 5. The Gabor mother wavelet is complex-valued, and has a real component (solid black) and an imaginary component (dashed) in the mother wavelet 5. The use of a complex-valued mother wavelet facilitates the extraction and representation of cardiac frequency magnitude and phase, based on a spatiotemporal reconstruction, e.g., using wavelets. The arrangement of FIG. 1 is repeated pixel-by-pixel across the image frames of an angiographic study to produce a cardiac space angiogram, which is a cine spatiotemporal representation of cardiac frequency phenomena in the angiogram. For clarity, the arrangement of FIG. 1 does not include other reconstruction steps that are executed in the computer program such as those that mitigate motion alias in balance with frequency alias in the reconstructed result.

Figure 2A:
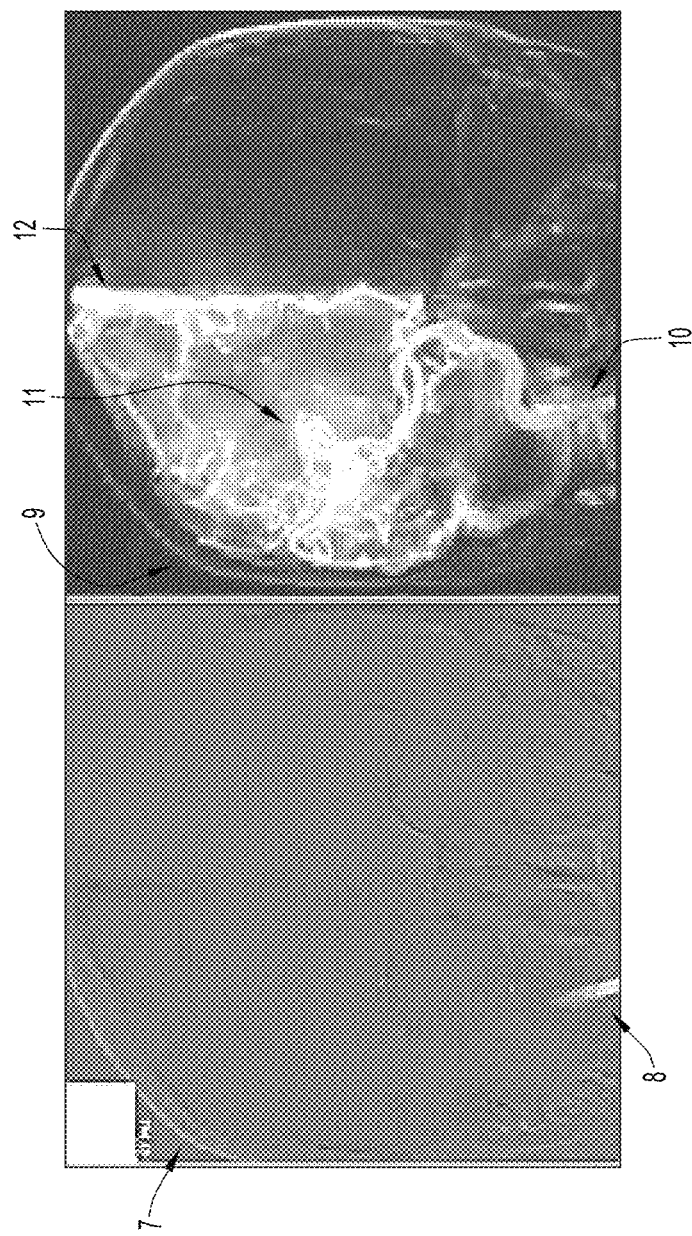
FIGS. 2A and 2B illustrate how the enabling discovery of the angiographic organization of cardiac frequency magnitude and phase, based on a spatiotemporal reconstruction, e.g., using wavelets, increases the angiographic informational yield while reducing risks and limitations and a corresponding hue brightness legend.

The arrangement in FIG. 2A shows an example angiogram and illustrates how the discovery may be exploited to lower intravascular contrast dose, enable the manufacture of lower footprint angiography hardware, and other desirable outcomes. FIG. 2A shows an image frame from a low dose conventional angiogram of the right internal carotid artery of the brain 7 and an image frame of a cardiac space angiogram corresponding to the same frame 9. At a low contrast and x-ray dose, right internal carotid artery 8 of the arterial subsystem is partially opacified but other circulatory subsystems are not opacified. In the image frame of a cardiac space angiogram corresponding to the same frame 9, several circulatory subsystems can be observed, including right internal carotid artery cardiac frequency phenomena 10, intervening vasculature between the right internal carotid artery cardiac frequency and the venous subsystem 11, and venous sub-system 12. Every pixel in the image represents a complex-valued datum. Each complex valued datum c may be rendered with a brightness-hue color model where cardiac frequency magnitude is rendered as brightness and phase as hue according to the legend brightness-hue legend 13. The anatomic demonstration of a relatively complete arterial subsystem, intervening subsystem, and venous sub-system in an image frame of a cardiac space angiogram corresponding to the same frame 9 reflects the additional informational yield from exploiting the informational yield of cardiac frequency angiographic phenomena. This extra informational yield serves as a biomarker for reducing the risk of angiography, for making it more efficient, and for facilitating the manufacture of lighter footprint angiography hardware.

Figure 3A:
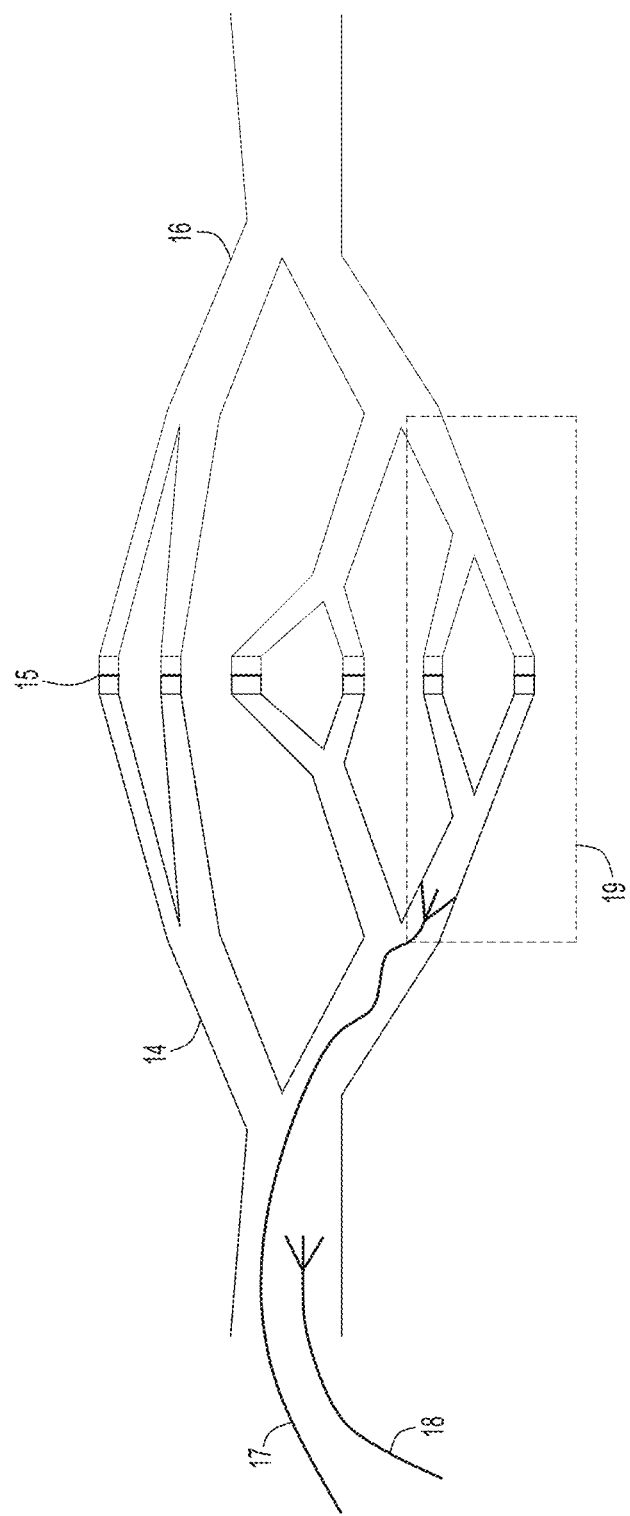

The arrangement in FIG. 3A depicts improvements in the benefit to risk profile of an angiography process offered by exploiting angiographic coherence. A vascular tree (19) contains an arterial subsystem 14, a capillary subsystem of the vascular tree 15, and venous subsystem of the vascular tree 16. There may be an injection catheter navigated distal into the vascular tree 17 (solid black) to inject a relatively smaller volume of intravascular chemical contrast agent and opacify a smaller portion of the vascular tree. There may be an injection catheter navigated proximal into the vascular tree 18 (dashed black) where a larger quantity of intravascular chemical contrast agent is injected to opacify a larger portion of the vascular tree. The injection catheter navigated distal into the vascular tree 17 produces a result where the travel allows greater discrimination of the arterial from venous subsystems. The injection catheter navigated proximal into the vascular tree 18 produces a result that reduces discrimination of the arterial from venous subsystems. The coherence at cardiac frequency between the arterial and venous subsystems provides a way to distinguish the arterial from venous subsystems other than by the travel timing of the passing contrast bolus. This allows those subsystems to be distinguished by a less sharp bolus injection and by a more safely placed proximal catheter, or even an injection from the venous system. Using the cardiac phenomenon described herein allows for methods where a distance from a catheter tip (black lines) to the capillary subsystem (15) of the vascular tree is significantly increased compared to a system that does not use the cardiac phenomenon. Exploiting the cardiac frequency signal in the injected contrast provides an increased signal to noise profile of all aspects of the angiogram, thereby allowing both intravascular chemical contrast dose and/or x-ray dose to be reduced. FIG. 3B shows a corresponding cardiac signal profile, showing magnitude 20 and phase 21.

Figure 4A:
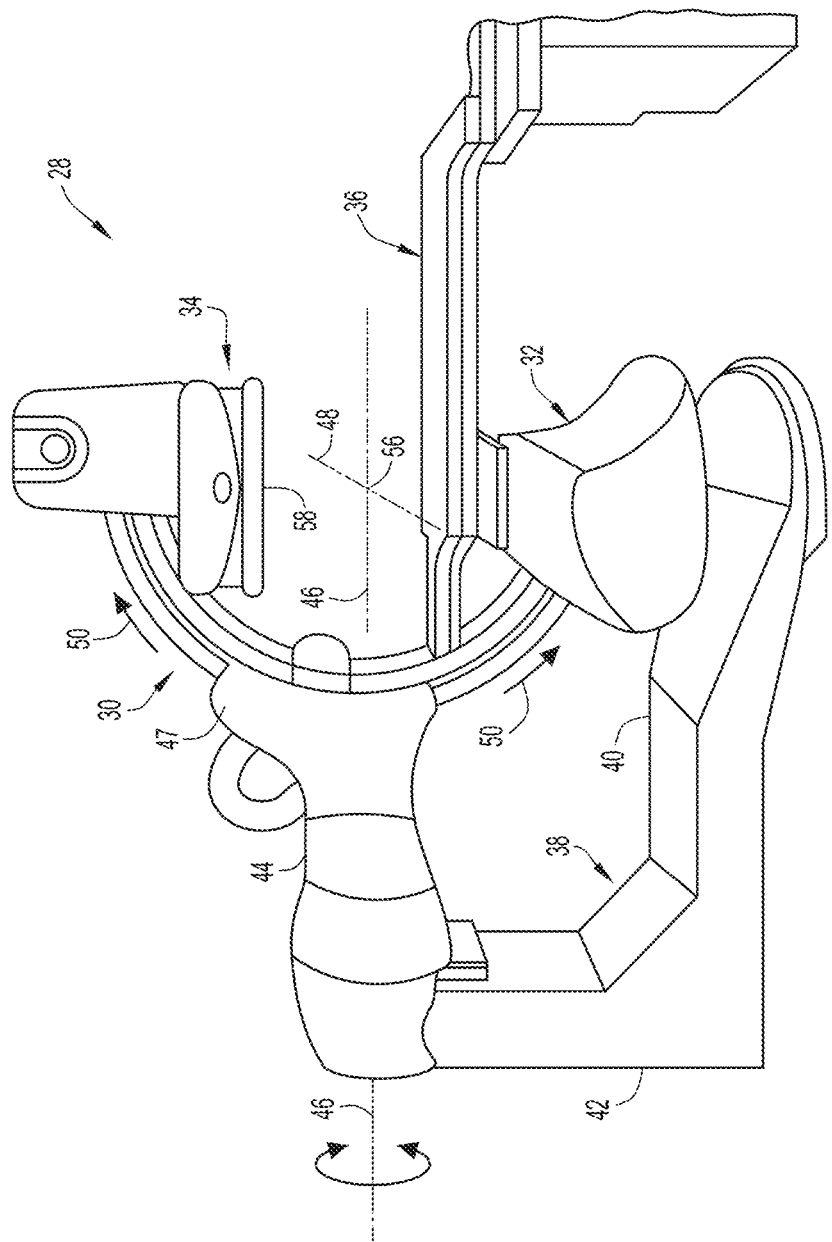
FIGS. 4A and 4B depict a rotational x-ray system that may be used with embodiments of the invention for acquiring angiographic data.
Figure 4B:
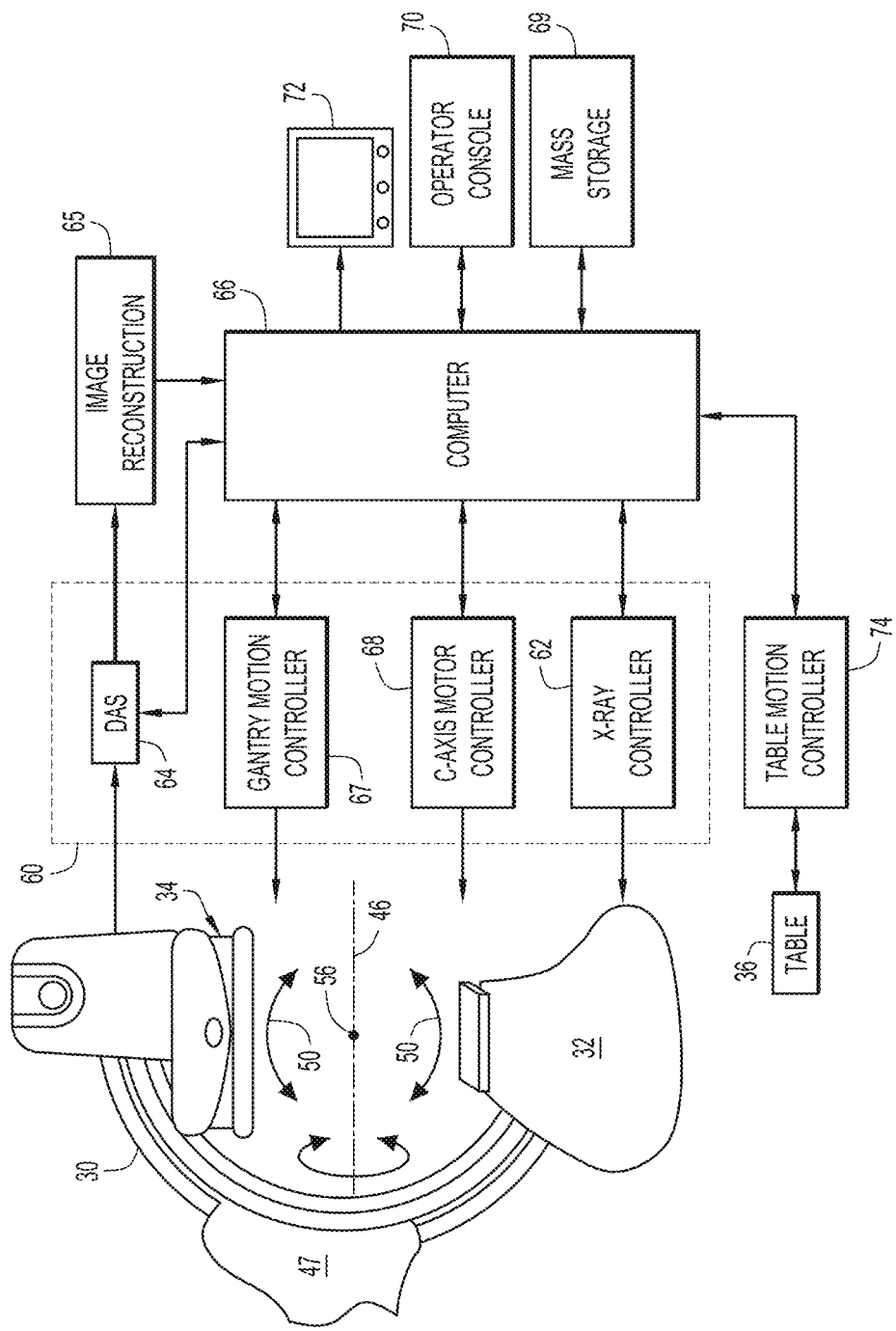

Referring to FIGS. 4A and 4B, a rotational x-ray system 28 is illustrated that may be used to obtain an angiogram at a faster than cardiac rate, such as via fluoroscopic angiography. As previously described, in acquiring an angiograph, a chemical contrast agent is injected into the patient and the contrast opacifies the vessels and allows their projections to be captured by the x-ray system as a two-dimensional image. However, the embodiments provided herein are not limited to two-dimensions, but may be applied to images acquired in three or more dimensions. A sequence of these two dimensional projection images is acquired that comprises an angiographic study—with the angiographic image frames acquired at faster than cardiac frequency to allow spatiotemporal reconstruction of the cardiac frequency phenomena into a cardiac space angiogram.

As shown in FIG. 4A, the rotational x-ray system 28 is characterized by a gantry having a C-arm 30 which carries an x-ray source assembly 32 on one of its ends and an x-ray detector array assembly 34 at its other end. The gantry enables the x-ray source 32 and detector 34 to be oriented in different positions and angles around a patient disposed on a table 36, while enabling a physician access to the patient. The gantry includes a pedestal 38 which has a horizontal leg 40 that extends beneath the table 36 and a vertical leg 42 that extends upward at the end of the horizontal leg 40 that is spaced from of the table 36. A support arm 44 is rotatably fastened to the upper end of vertical leg 42 for rotation about a horizontal pivot axis 46.

The pivot axis 46 is aligned with the centerline of the table 36, and the arm 44 extends radially outward from the pivot axis 46 to support a C-arm drive assembly 47 on its outer end. The C-arm 30 is slidably fastened to the drive assembly 47 and is coupled to a drive motor (not shown) which slides the C-arm 30 to revolve it about a C-axis 48 as indicated by arrows 50. The pivot axis 46 and C-axis 48 intersect each other, at an isocenter 56 located above the table 36, and are perpendicular to each other.

The x-ray source assembly 32 is mounted to one end of the C-arm 30 and the detector array assembly 34 is mounted to its other end. The x-ray source 32 emits a beam of x-rays which are directed at the detector array 34. Both assemblies 32 and 34 extend radially inward to the pivot axis 46 such that the center ray of this beam passes through the system isocenter 56. The center ray of the beam thus can be rotated about the system isocenter around either the pivot axis 46 or the C-axis 48, or both, during the acquisition of x-ray attenuation data from a subject placed on the table 36.

The x-ray source assembly 32 contains an x-ray source which emits a beam of x-rays when energized. The center ray passes through the system isocenter 56 and impinges on a two-dimensional flat panel digital detector 58 housed in the detector assembly 34. The detector 58 may be, for example, a 2048×2048 element two-dimensional array of detector elements. Each element produces an electrical signal that represents the intensity of an impinging x-ray and hence the attenuation of the x-ray as it passes through the patient. During a scan, the x-ray source assembly 32 and detector array assembly 34 are rotated about the system isocenter 56 to acquire x-ray attenuation projection data from different angles. The detector array is able to acquire 50 projections, or views, per second which is the limiting factor that determines how many views can be acquired for a prescribed scan path and speed.

Referring to FIG. 4B, the rotation of the assemblies 32 and 34 and the operation of the x-ray source are governed by a control mechanism 60 of the x-ray system. The control mechanism 60 includes an x-ray controller 62 that provides power and timing signals to the x-ray source 32. A data acquisition system (DAS) 64 in the control mechanism 60 samples data from detector elements and passes the data to an image reconstructor 65. The image reconstructor 65 receives digitized x-ray data from the DAS 64 and performs high speed image reconstruction according to the methods of the present disclosure. The reconstructed image is applied as an input to a computer 66 which stores the image in a mass storage device 69 or processes the image further.

The control mechanism 60 also includes gantry motor controller 67 and a C-axis motor controller 68. In response to motion commands from the computer 66, the motor controllers 67 and 68 provide power to motors in the x-ray system that produce the rotations about respective pivot axis 46 and C-axis 48. The computer 66 also receives commands and scanning parameters from an operator via console 70 that has a keyboard and other manually operable controls. An associated display 72 allows the operator to observe the reconstructed image and other data from the computer 66. The operator supplied commands are used by the computer 66 under the direction of stored programs to provide control signals and information to the DAS 64, the x-ray controller 62 and the motor controllers 67 and 68. In addition, computer 66 operates a table motor controller 74 which controls the motorized table 36 to position the patient with respect to the system isocenter 56.

Referring now to FIG. 5, a block diagram of a computer system or information processing device 80 is illustrated that may be used with rotational x-ray system 28 of FIGS. 4A and 4B for the extraction of cardiac frequency phenomena and the exploitation of cardiac frequency phenomena as biomarkers of properties of circulatory anatomy and physiology, according to an embodiment of the present invention.

FIG. 5 is merely illustrative of a general-purpose computer system 80 programmed according to techniques within this disclosure or a specific information processing device for an embodiment incorporating an invention whose teachings may be presented herein and does not limit the scope of the invention. One of ordinary skill in the art will recognize that other variations, modifications, and alternatives to computer system 80 may be used.

In one embodiment, computer system 80 includes monitor 82, computer 84 (which includes processor(s) 86, bus subsystem 88, memory subsystem 90, and disk subsystem 92), user output devices 94, user input devices 96, and communications interface 98. Monitor 82 can include hardware and/or software elements configured to generate visual representations or displays of information. Some examples of monitor 82 may include familiar display devices, such as a television monitor, a cathode ray tube (CRT), a liquid crystal display (LCD), or the like. In some embodiments, monitor 82 may provide an input interface, such as incorporating touch screen technologies.

Figure 2B:
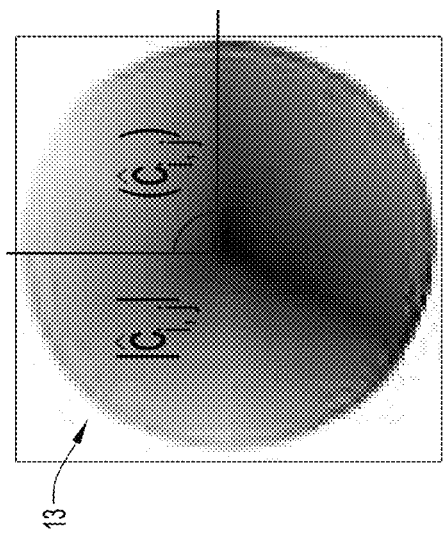

Computer 84 can include familiar computer components, such one or more central processing units (CPUs), memories or storage devices, graphics processing units (GPUs), communication systems, interface cards, or the like. As shown in FIG. 2, computer 84 may include one or more processor(s) 86 that communicate with a number of peripheral devices via bus subsystem 88. Processor(s) 86 may include commercially available central processing units or the like. Bus subsystem 88 can include mechanisms for letting the various components and subsystems of computer 84 communicate with each other as intended. Although bus subsystem 88 is shown schematically as a single bus, alternative embodiments of the bus subsystem may utilize multiple bus subsystems. Peripheral devices that communicate with processor(s) 86 may include memory subsystem 90, disk subsystem 92, user output devices 94, user input devices 96, communications interface 98, or the like.

Memory subsystem 90 and disk subsystem 92 are examples of physical storage media configured to store data. Memory subsystem 90 may include a number of memories including random access memory (RAM) for volatile storage of program code, instructions, and data during program execution and read only memory (ROM) in which fixed program code, instructions, and data are stored. Disk subsystem 92 may include a number of file storage systems providing persistent (non-volatile) storage for programs and data. Other types of physical storage media include floppy disks, removable hard disks, optical storage media such as CD-ROMS, DVDs and bar codes, semiconductor memories such as flash memories, read-only-memories (ROMS), battery-backed volatile memories, networked storage devices, or the like.

Memory subsystem 90 and disk subsystem 92 may be configured to store programming and data constructs that provide functionality or features of techniques discussed herein. Software code modules and/or processor instructions that when executed by processor(s) 86 implement or otherwise provide the functionality may be stored in memory subsystem 90 and disk subsystem 92.

User input devices 94 can include hardware and/or software elements configured to receive input from a user for processing by components of computer system 80. User input devices can include all possible types of devices and mechanisms for inputting information to computer system 84. These may include a keyboard, a keypad, a touch screen, a touch interface incorporated into a display, audio input devices such as microphones and voice recognition systems, and other types of input devices. In various embodiments, user input devices 94 can be embodied as a computer mouse, a trackball, a track pad, a joystick, a wireless remote, a drawing tablet, a voice command system, an eye tracking system, or the like. In some embodiments, user input devices 94 are configured to allow a user to select or otherwise interact with objects, icons, text, or the like that may appear on monitor 82 via a command, motions, or gestures, such as a click of a button or the like.

User output devices 96 can include hardware and/or software elements configured to output information to a user from components of computer system 80. User output devices can include all possible types of devices and mechanisms for outputting information from computer 84. These may include a display (e.g., monitor 82), a printer, a touch or force-feedback device, audio output devices, or the like.

Communications interface 98 can include hardware and/or software elements configured to provide unidirectional or bidirectional communication with other devices. For example, communications interface 98 may provide an interface between computer 84 and other communication networks and devices, such as via an internet connection.

FIG. 5 is representative of a computer system capable of embodying the present invention. It will be readily apparent to one of ordinary skill in the art that many other hardware and software configurations are suitable for use with the present invention. For example, the computer may be a desktop, portable, rack-mounted or tablet configuration. Additionally, the computer may be a series of networked computers. In still other embodiments, the techniques described above may be implemented upon a chip or an auxiliary processing board.

The usefulness of vascular coherence in wavelet angiography is demonstrated in the Example below, in which greatly reduced dosage of both contrast agent and x-ray radiation was used while providing improved diagnostic information.

Example

Two human angiograms were performed in immediate succession in anteroposterior (AP) projection of the right vertebral artery. Since iodinated contrast and x-ray have injurious properties, a so-called "puff" angiogram (preparatory angiogram) was obtained using 10% of the dose of the iodinated contrast agent and 1% of the x-ray dose conventionally used for a diagnostic angiogram.

For the "puff" injection the chemical agent used was iopamidol (Isovue), at a dose of 1 ml of a formulation of 3 mg/ml, which provides a dose of 3 mg iopamidol for the injection. The x-ray dose area product was 1.968 Gray m$^2$. The "dose area product" is a measure of the absorbed dose per kilogram multiplied by the area irradiated. The x-ray dose is obtained from the image series DICOM metadata.

For the regular ("full dose") right vertebral artery injection, the injected contrast dose was also iopamidol, but using 10 ml of the same formulation of 3 mg/ml, providing a dose of 30 mg iopamidol for the injection. The x-ray dose product was 156.876 Gray m$^2$.

The puff injection therefore used 10% of the dose of the iopamidol chemical contrast dose and 1.3% of the x-ray dose.

Figure 6:
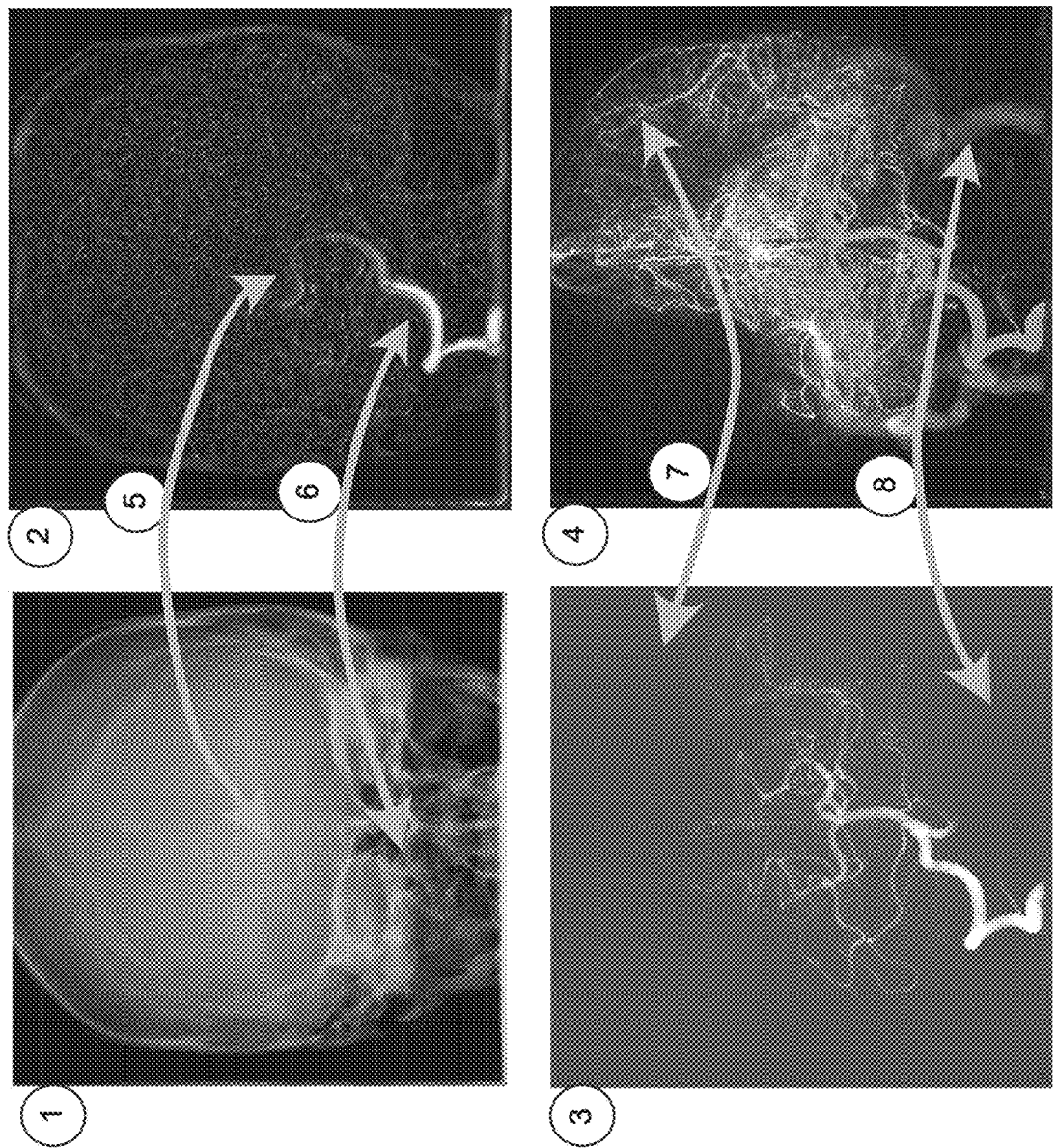
FIG. 6 shows a comparison of angiograms obtained with: (1) low contrast agent dose and low x-ray dose, with no wavelet reconstruction; (2) low contrast agent dose and low x-ray dose, with wavelet reconstruction; (3) conventional contrast agent dose and conventional x-ray dose, with no wavelet reconstruction; and (4) conventional contrast agent dose and conventional x-ray dose, with wavelet reconstruction.

The results obtained are shown in the top row (1 and 2) of FIG. 6. A puff angiogram typically is used to verify the correct position of a subject's body between the x-ray emitted tube and the x-ray detector, and to verify the integrity of the iodinated contrast injection catheters. A full angiogram of the same subject, using the conventional doses of contrast reagent and x-ray radiation is shown in the bottom row (3 and 4) of FIG. 6.

In the top left puff angiogram (1) the data are shown without wavelet reconstruction. The left arrow head of the double-headed arrow (5) shows a trace of contrast in a cerebral blood vessel. The finding of this vessel means that the subject is ready and appropriately situated for delivery of the full iodinated contrast dose through the injection catheter and the application of full x-ray dose (3)(also shown without wavelet reconstruction).

The angiogram (1) obtained without wavelet reconstruction can be compared to the angiogram (2) obtained with wavelet reconstruction. One vessel indicated by the double-headed arrow (5) can be seen with and without wavelet reconstruction—the left arrowhead shows the image without wavelet reconstruction, while the right arrowhead shows the superior image with wavelet reconstruction. The bones of the skull base in the conventional puff angiogram (1) block sufficient passage of x-rays to view the passage of the vessel across the skull base. Hence, a vessel indicated by the left arrow head of double-headed arrow (6) is not clearly seen.

By contrast, the puff angiogram with wavelet reconstruction shows the passage of the vessel through the skull base (right arrow head of double-headed arrow (6)). This is because those image pixels are varying in intensity at cardiac frequency, even though in a given image frame they do not have enough x-ray attenuation contrast to be seen in the conventional puff image (1).

The bottom row (3) and (4) of FIG. 6 shows the angiogram at conventional iodinated contrast and x-ray doses (3) and its wavelet reconstruction (4). The wavelet angiogram (4) shows arteries (double-headed arrow (7)) and veins (double-headed arrow (8)) that are not visible in the conventional angiogram (3).

Other objects, features and advantages of the methods described herein will be apparent from the detailed description. It should be understood, however, that the detailed descriptions provided herein are given by way of illustration only, since various changes and modifications within the spirit and scope of the invention will become apparent to those skilled in the art.

What is claimed is:

1. A method of imaging a mammalian host, comprising:
    acquiring angiographic data of the host at faster than cardiac frequency with a reduced dosage of contrast agent;
    processing the angiographic data obtained with the reduced dosage of the contrast agent is to generate a spatiotemporal reconstruction of cardiac frequency angiographic phenomena from the angiographic data, wherein the processing includes filtering for cardiac frequency; and
    generating a series of diagnostically useful images based on the processed angiographic data, wherein a diagnostically useful image is an image in which a minimum attenuation difference between a target tissue and surrounding tissue and fluids is a factor of two times;
    wherein the contrast agent is a chemical compound, a full dosage of the contrast agent is a minimum amount of the chemical compound required to obtain diagnostically useful images in an absence of generating the spatiotemporal reconstruction of cardiac frequency angiographic phenomena, and the reduced dosage of said contrast agent is at least 25% less than the full dosage.

2. The method according to claim 1, wherein the imaging is x-ray imaging.

3. The method according to claim 1, wherein the contrast agent is an iodine-containing imaging agent.

4. The method according to claim 3, wherein the contrast agent is a non-ionic iodine-containing imaging agent.

5. The method according to claim 1, wherein the contrast agent is a gadolinium-containing imaging agent.

6. The method according to claim 1, wherein the reduced dosage of said contrast agent is at least 50% less than the full dosage.

7. The method according to claim 1, wherein the reduced dosage of said contrast agent is at least 75% less than the full dosage.

8. The method according to claim 1, wherein the series of diagnostically useful images comprising the spatiotemporal reconstruction of cardiac frequency angiographic phenomena, comprises an image of a heart of the host.

9. The method according to claim 1, wherein the series of diagnostically useful images comprising the spatiotemporal reconstruction of cardiac frequency angiographic phenomena, comprises an image of part or all of a heart of the host.

10. The method according to claim 1, wherein the series of diagnostically useful images comprising the spatiotemporal reconstruction of cardiac frequency angiographic phenomena, comprises an image of part or all of a kidney of the host.

11. The method according to claim 1, wherein the series of diagnostically useful images comprising the spatiotemporal reconstruction of cardiac frequency angiographic phenomena, comprises an image of part or all of a cranium of the host.

12. The method according to claim 1, wherein the series of diagnostically useful images comprising the spatiotemporal reconstruction of cardiac frequency angiographic phenomena, comprises an image of part or all of a brain, a neck, a heart, a chest, an abdomen, a pelvis, legs, feet, arms or hands of the host.

13. A method of imaging a mammalian host, comprising:
    acquiring angiographic data of the host at faster than cardiac frequency using an x-ray dosage that is reduced in comparison with a full x-ray dosage and an amount of contrast agent;
    processing the angiographic data obtained with the reduced x-ray dosage to generate a spatiotemporal reconstruction of cardiac frequency angiographic phenomena from the angiographic data, wherein the processing includes filtering for cardiac frequency; and
    generating a series of angiographic images based on the processed angiographic data;
    wherein the full x-ray dosage is a minimum amount of x-ray radiation required to achieve, with the amount of the contrast agent, an attenuation difference between a target tissue and surrounding tissue and fluids by a factor of two times in an absence of generating the spatiotemporal reconstruction of cardiac frequency angiographic phenomena, and wherein the reduced x-ray dosage is at least 25% less than the full x-ray dosage.

14. The method according to claim 13, wherein the reduced x-ray dosage is at least 50% less, or at least 75% less than the full x-ray dosage.

15. The method of claim 1, wherein the spatiotemporal reconstruction includes a wavelet reconstruction.

16. The method of claim 1, wherein generating includes rendering the series of diagnostically useful images as a motion cine.

17. The method of claim 1, further comprising storing the series of diagnostically useful images as a video file format.

18. The method of claim 13, wherein generating includes rendering the series of angiographic images as a motion cine.

19. The method of claim 13, further comprising storing the series of angiographic images as a video file format.

20. The method of claim 1, wherein the contrast agent is an iodinated chemical contrast agent selected from the group consisting of iohexol, iopromide, iodixanol, ioxaglate, iothalamate, and iopamidol.

21. The method of claim 13, wherein the contrast agent is an iodinated chemical contrast agent selected from the group consisting of iohexol, iopromide, iodixanol, ioxaglate, iothalamate, and iopamidol.

* * * * *